(12) United States Patent
Zambaldi et al.

(10) Patent No.: US 11,141,509 B2
(45) Date of Patent: Oct. 12, 2021

(54) METHOD FOR LOADING AT LEAST TWO POWDER SUBSTANCES INTO RECESSES PROVIDED AT A STENT SURFACE

(71) Applicant: CID S.p.A., Saluggia (IT)

(72) Inventors: Ilaria Zambaldi, Ivrea (IT); Franco Vallana, Turin (IT); Matteo Antoniotti, Settimo Torinese (IT); Andrea Grignani, Chieri (IT)

(73) Assignee: CID S.P.A., Saluggia (IT)

( * ) Notice: Subject to any disclaimer, the term of this patent is extended or adjusted under 35 U.S.C. 154(b) by 124 days.

(21) Appl. No.: 16/089,058

(22) PCT Filed: Mar. 28, 2017

(86) PCT No.: PCT/IB2017/051764
§ 371 (c)(1),
(2) Date: Sep. 27, 2018

(87) PCT Pub. No.: WO2017/168319
PCT Pub. Date: Oct. 5, 2017

(65) Prior Publication Data
US 2019/0091378 A1  Mar. 28, 2019

(30) Foreign Application Priority Data
Mar. 29, 2016  (IT) .................. 102016000032217

(51) Int. Cl.
*B29C 43/18* (2006.01)
*A61L 31/16* (2006.01)
(Continued)

(52) U.S. Cl.
CPC ............. *A61L 31/16* (2013.01); *A61L 31/022* (2013.01); *A61L 31/08* (2013.01); *A61L 31/084* (2013.01);
(Continued)

(58) Field of Classification Search
None
See application file for complete search history.

(56) References Cited

U.S. PATENT DOCUMENTS 5,443,458 A    8/1995  Eury
8,067,054 B2 *  11/2011  Weber ................... A61F 2/915
                                                264/260

(Continued)

FOREIGN PATENT DOCUMENTS

CN    1256628 A      6/2000
EP    1 994 950 A2  11/2008
(Continued)

OTHER PUBLICATIONS

Jan. 12, 2012 PCT Search Report for International Application No. PCT/IB2011/054092 (12 pages).
(Continued)

*Primary Examiner* — Edmund H Lee
(74) *Attorney, Agent, or Firm* — Nixon & Vanderhye, PC

(57) ABSTRACT

In an embodiment, a method for loading a powder substance (10) into recesses (200) provided at a stent (S) surface, the method comprises:
  applying compression (100) to the powder substance (10) to thereby form tablets insertable into said recesses (200),
  inserting the tablets into the recesses (200) of the stent (S).

13 Claims, 18 Drawing Sheets

(51) Int. Cl.
  *A61L 31/08* (2006.01)
  *B29C 43/20* (2006.01)
  *A61L 31/02* (2006.01)

(52) U.S. Cl.
  CPC .............. *B29C 43/18* (2013.01); *B29C 43/20* (2013.01); *A61L 2300/216* (2013.01); *A61L 2300/41* (2013.01); *A61L 2300/416* (2013.01); *A61L 2300/62* (2013.01); *A61L 2420/02* (2013.01); *A61L 2420/04* (2013.01); *A61L 2420/06* (2013.01)

(56) References Cited

U.S. PATENT DOCUMENTS

| | | | | |
|---|---|---|---|---|
| 8,070,797 | B2* | 12/2011 | Flanagan | A61L 31/082 623/1.1 |
| 8,353,949 | B2* | 1/2013 | Weber | A61F 2/82 427/2.25 |
| 8,574,615 | B2* | 11/2013 | Tenney | A61F 2/91 424/423 |
| 9,011,898 | B2 | 4/2015 | Curcio et al. | |
| 2004/0208985 | A1 | 10/2004 | Rowan et al. | |
| 2005/0245637 | A1 | 11/2005 | Hossainy et al. | |
| 2006/0002977 | A1* | 1/2006 | Dugan | A61K 31/573 424/426 |
| 2006/0095123 | A1* | 5/2006 | Flanagan | A61L 31/16 623/1.46 |
| 2007/0202149 | A1 | 8/2007 | Faucher et al. | |
| 2012/0089122 | A1* | 4/2012 | Lee | A61L 29/16 604/517 |
| 2012/0323312 | A1 | 12/2012 | Curcio et al. | |
| 2013/0280315 | A1* | 10/2013 | Curcio | A61L 31/16 424/423 |
| 2015/0297870 | A1 | 10/2015 | Minoletti et al. | |
| 2019/0117852 | A1 | 4/2019 | Zambaldi et al. | |
| 2019/0125940 | A1 | 5/2019 | Zambaldi et al. | |

FOREIGN PATENT DOCUMENTS

| | | |
|---|---|---|
| WO | WO 03/035134 A1 | 5/2003 |
| WO | WO 2005/013936 A2 | 2/2005 |
| WO | WO 2017/168314 A1 | 10/2017 |
| WO | WO 2017/168317 A1 | 10/2017 |

OTHER PUBLICATIONS

Translation for CN1256628A (23 pages).
Jun. 9, 2017 PCT Search Report for International Application No. PCT/IB2017/051761 (12 pages).
Jun. 9, 2017 PCT Search Report for International Application No. PCT/IB2017/051758 (11 pages).
Jun. 9, 2017 PCT Search Report for International Application No. PCT/IB2017/051764 (12 pages).
PubChem, Sirolimus, Dec. 10, 2019, pp. 1 to 100 (Year: 2019).
Non-Final Office Action issued in U.S. Appl. No. 16/088,983 dated Oct. 15, 2019.
Final Office Action issued in U.S. Appl. No. 16/088,983 dated Mar. 3, 2020.
Non-Final Office Action issued in U.S. Appl. No. 16/089,013 dated Dec. 17, 2019.
Final Office Action issued in U.S. Appl. No. 16/089,013 dated Jun. 2, 2020.
Non-Final Office Action dated May 19, 2021 in co-pending U.S. Appl. No. 16/089,013, first inventor Zambaldi, 371(c) date Sep. 27, 2018.

* cited by examiner

METHOD FOR LOADING AT LEAST TWO POWDER SUBSTANCES INTO RECESSES PROVIDED AT A STENT SURFACE

TECHNICAL FIELD

The present description concerns stents.

One or more embodiments may refer to stents capable of releasing active principles to the site of implantation to counteract the phenomenon of restenosis.

TECHNOLOGICAL BACKGROUND

Implantation devices, such as, for example stents, can be used when the lumen of an artery undergoes a narrowing, for example, caused by an obstruction. This obstruction leads to a decrease in blood flow and can cause ischemic phenomena.

The stent is a cylindrical metal structure that is introduced into the artery lumen and is made to expand at the level of the obstruction, e.g. until its diameter is approximately that of the original vessel. In this way, the narrowing of the vessel is reduced, that is the stenosis is reduced, both in the acute phase and the long-term phase.

Over the years, the main function of the stent, as a mechanical support of the vessel, has been joined by a pharmacological action aimed at reducing the incidence of a phenomenon known as restenosis, which consists in the partial or total re-occlusion of the vessel.

The association of active principles with implantation devices, with the object of limiting restenosis is a well-established technique.

A typical example is represented by the so-called Drug Eluting Stents (DESs), namely stents that carry substances such as pharmaceutical agents that are antagonists of restenosis at the stent implantation site.

An active principle can be loaded onto implantable devices using compounds that act as carriers of the active principle and modulate its release at the implantation site.

Although polymeric constituents have been used as carriers for the release of the active principle starting from, for example, coronary stents, currently various motives of perplexity have been raised about the safety of these materials.

For example, polymeric substances applied on an implantable device can remain in situ for very long periods of time, thus undesirably disturbing or changing the healing process of the implantation site. This effect can be exacerbated by an incomplete release of the drug from the carrier.

These adverse reactions even exist in the case in which biodegradable polymers are used as carriers. Indeed, the presence of the polymer always remains beyond the diffusion period of the active principle, and introduces the possibility of cytotoxic or inflammatory effects related to the in situ degradation of the polymeric carrier (for example, to the degradation of polyester-based polymers).

Compositions that are not polymeric in nature have been used for the release of active principles, for example, in the form of esters of fatty acids of polyalcohols, sugars or vitamins, as described in the European Patent EP-B-1994950 or in the form of fatty acids as described in the European patent EP-B-1449546.

These compositions have made it possible to accurately control the release of the active principle loaded onto the stent, avoiding the production of drug concentration peaks in the initial release phase, avoiding local toxic effects.

The phenomenon of restenosis is, however, a very complex biological phenomenon involving many biological reactions of an inflammatory nature and cell hyperproliferation resulting in the formation of a hyperplastic neointima at the stent implantation site.

The inflammation is mainly caused by the reaction of endothelial cells that have undergone physical damage due to the expansion of the stent at the implantation site. In particular, at the stent implantation site, a platelet thrombus can form (also referred to as mural thrombus) on the damaged vessel wall, which in turn gives rise to an inflammatory process with activation, adhesion, aggregation and deposition of additional platelets and neutrophils. The mural thrombus is covered with a layer of endothelial-like cells within a few days, and begins an intense infiltration of monocytes and lymphocytes with release of additional inflammatory factors such as cytokines and chemokines. These cells migrate successively deeper into the mural thrombus in the vessel wall, which is followed by a phase of cell activation, proliferation and formation of extracellular matrix (cell hyperproliferation phase). In this phase, the smooth muscle cells of the vascular wall begin to proliferate, reabsorbing the mural thrombus and causing a thickening of the neointima, which becomes hyperplastic.

To date, there are no stents that are able to effectively counteract the inflammatory phenomena and cell hyperproliferation, which are triggered at the stent implantation site following implantation of the stent, with consequent formation of a hyperplastic neointima.

OBJECT AND SUMMARY

Bearing in mind these premises, there is therefore a need to deliver improved solutions enabling the provision of stents capable of overcoming the disadvantages of the prior art.

According to one or more embodiments, this object can be achieved thanks to that which is specifically recalled in the attached claims, which form an integral part of the present description.

For example, in one or more embodiments, a stent may be provided capable of releasing—in a controlled manner—at least one first and one second active principle for treating the stent implantation site, where said at least one first and one second active principle are loaded on at least one portion of the stent surface in a layered configuration comprising at least one first and one second layer, which are different from each other and selected from anti-proliferative drugs and anti-inflammatory drugs, respectively, the first layer being formed on at least one portion of the stent surface and comprising the at least one first active principle and at least one or more first excipients, and the second layer being formed on the first layer and comprising the at least one second active principle and at least one or more second excipients, wherein said at least one or more first excipients are selected from fatty acids having a linear or branched saturated chain, comprising a number of carbon atoms from 16 to 34, and said at least one or more second excipients are selected from fatty acids having a linear or branched saturated chain, comprising a number of carbon atoms from 4 to 18 and wherein said at least one or more first excipients or a mixture thereof has/have a melting temperature higher than the melting temperature of said at least one or more second excipients or a mixture thereof.

Again for example, in one or more embodiments, it is possible to provide a method for producing a stent capable of releasing at least one first and one second active principle at the stent implantation site, the at least one first and one second active principle being different from each other and being selected from anti-proliferative drugs and anti-inflammatory drugs, respectively, wherein the method involves the following steps:

i) providing a first powder formulation comprising said at least one first active principle and at least one or more first excipients selected from fatty acids having a linear or branched saturated chain, comprising a number of carbon atoms between 16 and 34;

ii) loading the first formulation onto at least one portion of the stent surface;

iii) subjecting the stent obtained in step ii) to a heat treatment at a temperature T1 for stabilizing the first formulation loaded on the stent;

iv) providing a second powder formulation comprising said at least one second active principle and at least one or more second excipients selected from fatty acids having a linear or branched saturated chain, comprising a number of carbon atoms between 4 and 18;

v) loading the stent obtained in step iii) with the second formulation on the same portion of the stent surface loaded with the first formulation;

vi) subjecting the stent obtained in step v) to a heat treatment at a temperature T2 for stabilizing the second formulation loaded on the stent;

wherein the temperature T1 is greater than the temperature T2, obtaining a stent loaded with said at least one first and one second active principles.

Still by way of example, in one or more embodiments, one or more (micro)tablet formulations can be loaded onto the stent, that is, as a powder formulation subjected to compression to obtain a tablet of known weight to be inserted into the recesses one by one.

This allows the dose loaded onto the stent to be increased and/or a finer control of the loading.

In one or more embodiments, it is possible to melt the individual tablets with a heated nitrogen micro-melter or with a hot metal probe.

The results reported below show that the stent described herein allows modulation of the release of the active principle with anti-proliferative activity and the active principle with anti-inflammatory activity in an accurate and temporally articulated manner in order to reduce the phenomenon of restenosis.

BRIEF DESCRIPTION OF THE FIGURES

One or more embodiments will be now described, by way of non-limiting example, with reference to the attached figures, wherein.

DETAILED DESCRIPTION OF SOME EXEMPLARY EMBODIMENTS

Figure 1:
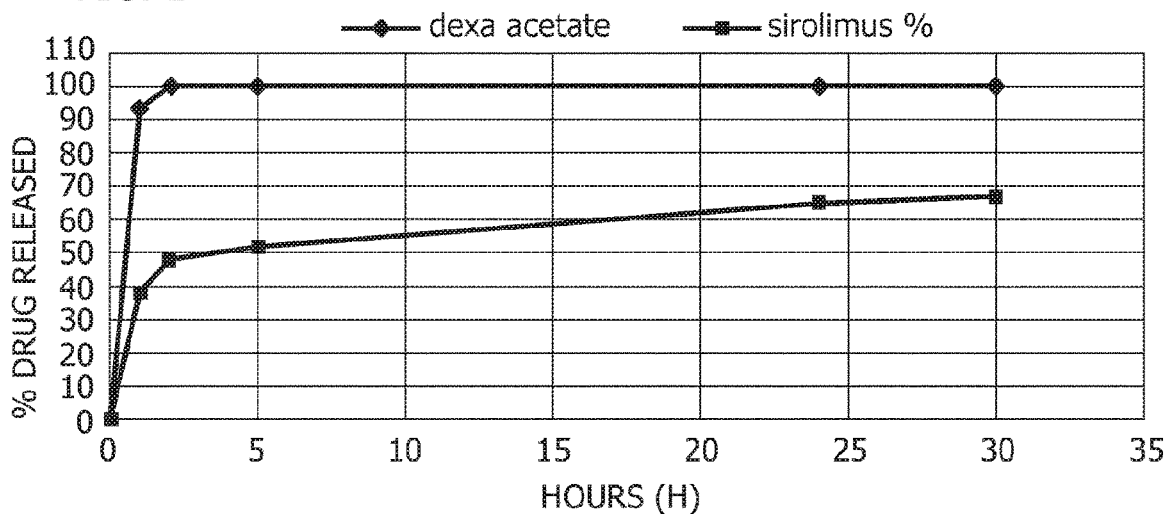
FIGS. 1 to 3 are diagrams representative of various release profiles of active substances loaded onto stents provided with recesses for the loading of these substances.

In the following description, there are numerous specific details to provide a thorough understanding of the embodiments. The embodiments may be implemented in practice without one or more of the specific details, or with other methods, components, materials, etc. In other cases, well-known structures, materials or operations are not shown or described in detail to avoid obscuring certain aspects of the embodiments.

Throughout the present specification, the reference to "an embodiment" or "embodiment" means that a particular configuration, structure, or characteristic described in connection with the embodiment is included in at least one embodiment. Therefore, the appearance of the phrases "in an embodiment" or "in a certain embodiment" in various sites throughout the entire present specification does not necessarily refer to the same embodiment. Moreover, the particular configurations, structures or characteristics can be combined in any convenient way in one or more embodiments.

The headings and references used here serve merely for convenience and do not interpret the object or meaning of the embodiments.

The production of stents capable of being loaded with active substances (e.g. active principles with anti-proliferative activity capable of being released with an antagonist effect of restenosis) constitutes an extended area of research.

For example, documents such as EP 0 850 604 A2, EP 1 277 449 A1, EP 1 310 242 A1, EP 1 561 436 A1 or EP 2 253 339 A1 exemplify the possibility of loading these active substances into recesses ("cavities") formed, e.g. by machining with a laser beam, on the outer surface of the stent. In particular, EP 1 561 436 A1 exemplifies the possibility of loading multiple layers of substances.

In one or more embodiments, the present description concerns a stent capable of releasing—in a controlled manner—at least one first and one second active principle for treating the stent implantation site, where said at least one first and one second active principles are loaded on at least one portion of the stent surface in a layered configuration comprising at least one first and one second layer, which are different from each other and selected from anti-proliferative drugs and anti-inflammatory drugs, respectively, the first layer being formed on at least one portion of the stent surface and comprising the at least one first active principle and at least one or more first excipients, and the second layer being formed on the first layer and comprising the at least one second active principle and at least one or more second excipients, wherein said at least one or more first excipients are selected from fatty acids having a linear or branched saturated chain, comprising a number of carbon atoms from 16 to 34, and said at least one or more second excipients are selected from fatty acids having a linear or branched saturated chain, comprising a number of carbon atoms from 4 to 18 and wherein said at least one or more first excipients or a mixture thereof has/have a melting temperature higher than the melting temperature of said at least one or more second excipients or a mixture thereof.

The stent subject of the present description is able to release the two active principles loaded on it at different times and specifically to release the active principle with anti-inflammatory activity in the first few days following the stent implantation and in the successive period, the active principle with anti-proliferative activity.

The Applicant considers, in fact, that this release profile of the two active principles allows more effective counteraction of the phenomenon of restenosis, with respect to that previously obtained with stents available on the market.

Without wishing to be bound to any theory in this regard, the Applicant believes that the reduction in the entity of the inflammatory process that occurs at the stent implantation site—due to the mechanical damage imparted by the stent to the endothelial cells forming the inner surface of the vessel—allows reduction of the subsequent cell hyperproliferation phenomenon and therefore the thickening of the neointima.

The Applicant has therefore produced a stent able to release at least one active principle with anti-inflammatory activity and at least one active principle with anti-proliferative activity with specific release kinetics of the two active principles, that is, firstly the active principle with anti-inflammatory activity and secondly the active principle with anti-proliferative activity.

It is believed, in fact, that the controlled release, first of all, of the anti-inflammatory active principle allows the interruption of the cascade of inflammatory factors (such as adhesion molecules, inflammatory cytokines, chemokines and metalloproteinases) intimately related to cellular hyperproliferative processes mainly dependent, but not exclusively, on smooth muscle cells. The subsequent release of the active principle with anti-proliferative activity thus exerts a more effective control on the physiological process of regeneration of the damaged vessel wall, counteracting the hyperproliferation of smooth muscle cells on the vessel wall that—if not controlled—leads to the formation of a hyperplastic neointima with the risk of a partial re-occlusion of the stent implantation site.

The different release kinetics of the two active principles loaded on the stent subject of the present description were obtained using excipients based on fatty acids with different physical characteristics (in particular, different melting temperatures) for each of the active principles.

Surprisingly, the Applicant has, in fact, discovered that the different melting temperatures of the one or more first excipients or the mixture thereof and the one or more second excipients or of the mixture thereof allows the active principle with anti-inflammatory activity to be released first and only after this is the active principle with anti-proliferative activity released, at a second period of time. In other words, the different melting temperatures of the one or more first excipients or the mixture thereof and the one or more second excipients or the mixture thereof, associated with the two active principles, allows the temporal setting of the solubilization of these excipients, making the anti-inflammatory active principle available first and subsequently the anti-proliferative active principle. In particular, the stent almost exclusively releases the active principle with anti-inflammatory activity in the first few days after implantation of the stent (about 1-5 days), and only then does it release the active principle with anti-proliferative activity, for a long period of time (up to 3-4 months after stent implantation). The investigation of the applicant has, in fact, demonstrated that a complete release of Sirolimus (anti-proliferative active principle) at 30 hours in the in vitro experimentation is related to an in vivo release after coronary implantation greater than 30 days (Eurointervention 2012; 7:1087-1094 "Cre8™ coronary stent:preclinical in vivo assessment of a new generation polymer-free DES with Amphilimus™ formulation")

Without wishing to be bound to any theory in this regard, the Applicant has reason to believe that the different melting temperatures of the one or more first excipients or the mixture thereof and the second one or more excipients or the mixture thereof, used to load the active principles onto the stent, affect the solubilization speed of these excipients making the dissolution kinetics substantially different.

In the solid state, the fatty acid molecules interact with each other through Van der Waals forces, which are separated in the solid-to-liquid transition. The energy needed to break these Van der Waals forces determines the melting point of these molecules.

It follows that for producing the first layer, the use of at least one or more first excipients or a mixture thereof having a higher melting temperature than the melting temperature of the at least one or more second excipients or the resulting mixture used to produce the second layer requires a higher energy to break the Van der Waals forces produced between the excipient molecules of the first layer compared to that needed to break the forces produced between the excipient molecules of the second layer.

The first excipient(s) and the second excipient(s), based on fatty acids, also allow the implementation of essentially homogenous structures on the stent, that is essentially free of molecular aggregates and/or cavities that would affect the release of the active principle in a negative way, and capable of adequately adhering on the stent surface.

Moreover, the first excipient(s) and the second excipient(s) being based on fatty acids give rise to formulations that can be layered on the outer and/or the inner surface of the stent or on portions of the stent surfaces represented, for example, by reservoirs or "recesses" present on these surfaces.

The weight ratio of the active principle:excipient(s) is adjustable to obtain the required release profile of the drug, in particular, in relation to the amount of released principle required to be therapeutically effective.

In an embodiment, the active principle with anti-inflammatory activity is present in a quantity, with respect to the first excipient(s) between 55 and 90% by weight, optionally between 65 and 90% by weight.

In an embodiment, the active principle with anti-proliferative activity is present in a quantity, with respect to the second excipient(s) between 45 and 55% by weight, optionally between 40 and 50% by weight.

In an optional embodiment, the at least one or more first excipients are selected from fatty acids having a linear or branched saturated chain, comprising a number of carbon atoms between 16 and 22.

In an optional embodiment, the at least one or more second excipients are selected from fatty acids having a linear or branched saturated chain, comprising a number of carbon atoms between 14 and 18.

In an optional embodiment, the first excipient essentially consists of stearic acid.

In an optional embodiment, the at least one or more second excipients essentially consist of stearic acid and palmitic acid mixed in a weight ratio between 40:60 and 60:40, optionally 50:50.

In an embodiment, the one or more first excipients or the mixture thereof has (have) a melting temperature between 68 and 80° C., optionally between 68 and 78° C.

In an embodiment, the one or more second excipients or the mixture thereof has (have) a melting temperature between 50 and 65° C., optionally between 54 and 60° C.

The active principles with anti-inflammatory activity are optionally selected from corticosteroids and glucocorticoids, e.g. from betamethasone, clobetasol, beclomethasone, budesonide, flunisolide, fluocinolone acetonide, dexamethasone, mometasone, prednisolone.

The active principles with anti-proliferative activity are optionally selected from compounds belonging to the class of immunosuppressants or to the anti-tumor class, e.g. from everolimus, tacrolimus, sirolimus, zotarolimus, biolimus, paclitaxel.

The release profiles of stents made in accordance with the present description show that a stent loaded with two formulations containing excipients based on fatty acids with different melting temperatures, that is, for the first layer between 68-80° C. (optionally between 68-78° C.) and for the second layer between 50-65° C. (optionally between 54-60° C.), is capable of releasing the active principles contained in the two layers with controlled kinetics, where the anti-inflammatory active principle (contained in the second layer) is released in a short time after the stent implantation and the anti-proliferative active principle (contained in the first layer) is released for a longer period for the effective inhibition of the growth of smooth muscle cells.

Figure 2:
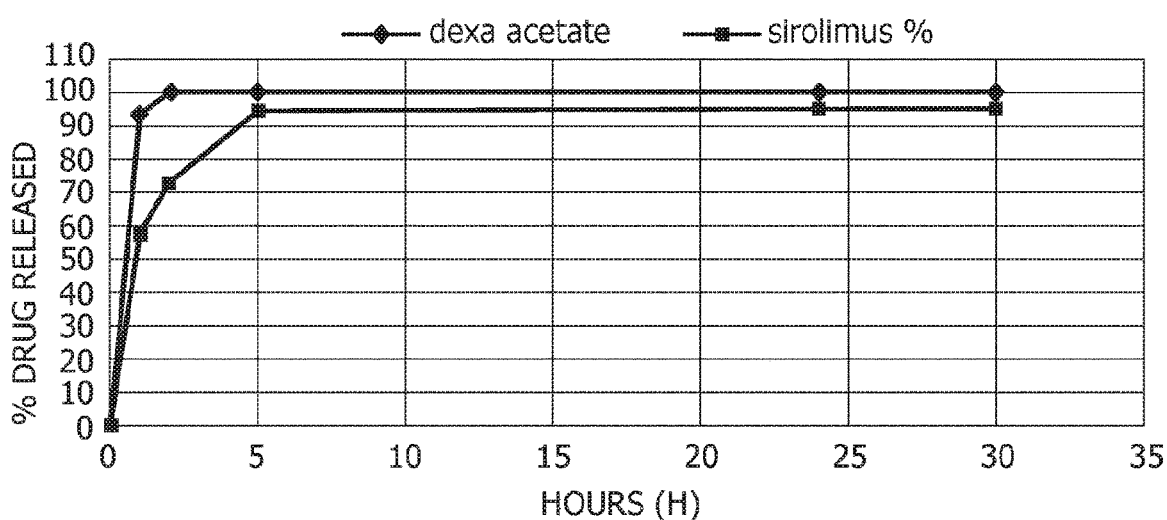

The reversal of the excipients in the production of the two layers (that is, the use of excipients with lower melting temperature for producing the first layer and excipients with higher melting temperature for producing the second layer) may not allow the control and the separation of the two kinetics: the two drugs are, in fact, both released with a similar kinetic profile that is less controlled (see for example FIG. 2).

In one or more embodiments, the present description concerns a method for producing a stent capable of releasing at least one first and one second active principle at the stent implantation site, the at least one first and one second active principles being different from each other and being selected from anti-proliferative drugs and anti-inflammatory drugs, respectively, wherein the method involves the following steps:

i) providing a first powder formulation comprising said at least one first active principle and at least one or more first excipients selected from fatty acids having a linear or branched saturated chain, comprising a number of carbon atoms between 16 and 34;

ii) loading the first formulation onto at least one portion of the stent surface;

iii) subjecting the stent obtained in step ii) to a heat treatment at a temperature T1 for stabilizing the first formulation loaded on the stent;

iv) providing a second powder formulation comprising said at least one second active principle and at least one or more second excipients selected from fatty acids having a linear or branched saturated chain, comprising a number of carbon atoms between 4 and 18;

v) loading the stent obtained in step iii) with the second formulation on the same portion of the stent surface loaded with the first formulation;

vi) subjecting the stent obtained in step v) to a heat treatment at a temperature T2 for stabilizing the second formulation loaded on the stent;

wherein the temperature T1 is greater than the temperature T2, obtaining a stent loaded with said at least one first and one second active principles.

In an optional embodiment, the temperature T1 is greater than the temperature T2 by at least 10° C.

In an embodiment, the temperature T1 can be between 68 and 80° C., optionally between 68 and 78° C.

In an embodiment, the temperature T2 can be between 50 and 65° C., optionally between 54 and 60° C.

In one or more embodiments, prior to conducting the step iii) and/or the step vi), the stent can be subjected to a cleaning operation of the surface in order to deposit said first layer only on at least one portion of the stent surface and/or in order to deposit said second layer only at said first layer.

In one or more embodiments, said at least one portion of the stent surface can be formed by recesses present on the surface of the stent.

In one embodiment, after conducting the heat treatment steps iii) and/or vi) the stent is subjected to a cooling step at room temperature. This (these) cooling operation(s) are conducted for a period of time between 1 and 10 minutes, optionally between 1 and 5 minutes.

The excipients used for loading the respective active principles on the stent allow the stent to be subjected to thermal treatments for stabilizing the formulations, so that they present a mechanical strength and a degree of adhesion to the surface of the stent and to the surface of the first formulation on which they have been deposited, adapted to the mechanical stresses suffered by the stent during transportation, storage and the insertion procedure in the patient and the expansion.

In particular, the heat treatment to which the two different formulations are subjected to allows solid formulations to be obtained in which both the active principle and excipients have assumed a crystalline structure, which further contributes to appropriately controlling the release of the active principle according to the required release kinetics. Indeed, it is known that solid formulations with amorphous structure do not allow an effective control of the release of the active principle, which dissolves fairly quickly into the bloodstream, with peaks of concentration of the active principle, harmful for treating the implantation site and being impossible to control the restenosis phenomenon in an effective manner.

In one or more embodiments, it is possible to envisage that the active principle with anti-inflammatory activity and the active principle with anti-proliferative activity are loaded into the recesses or cavities of the stent, with the active principle with anti-inflammatory activity localized at the mouth portion of the loading recess or cavity, and the active principle with anti-proliferative activity localized at the bottom portion of the recess or cavity.

EXAMPLES

The stents used in the present experiments are chromocobalt stents coated with a thin film of turbostratic pure carbon (Carbofilm™), where this film increases the biocompatibility and the thrombus resistance of the stent.

The stents have reservoirs on their outer surface, in the form of recesses, able to contain a first and a second active principle loaded within the recesses in a layered configuration using respective first and second excipients selected from linear or branched saturated fatty acids having different melting temperatures from each other.

Hereinafter the operational details will be provided for producing different pairs of formulations, and the respective loading onto a stent in the aforesaid layered configuration.

Figure 3:
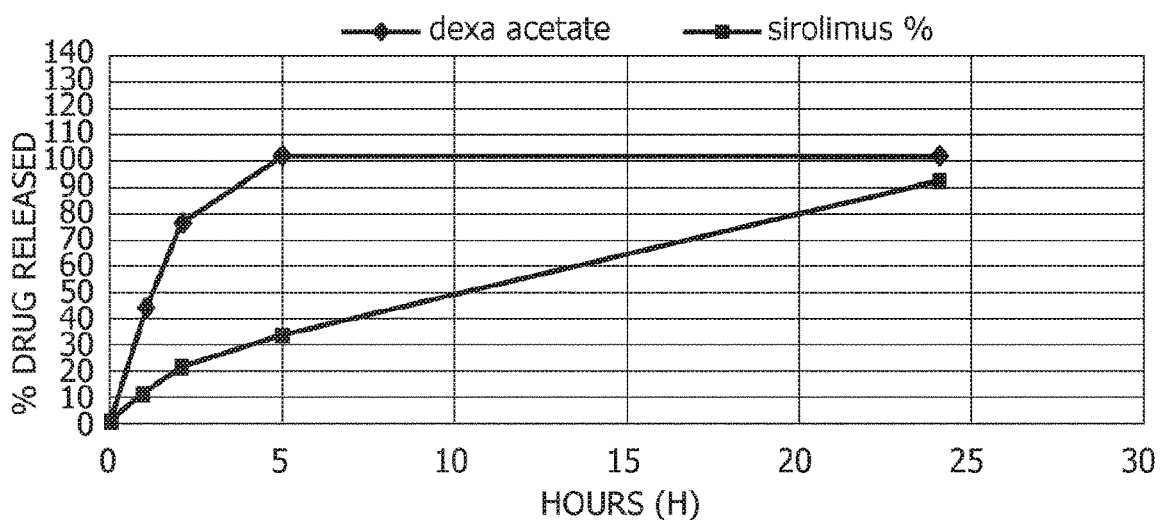
Figure 15:
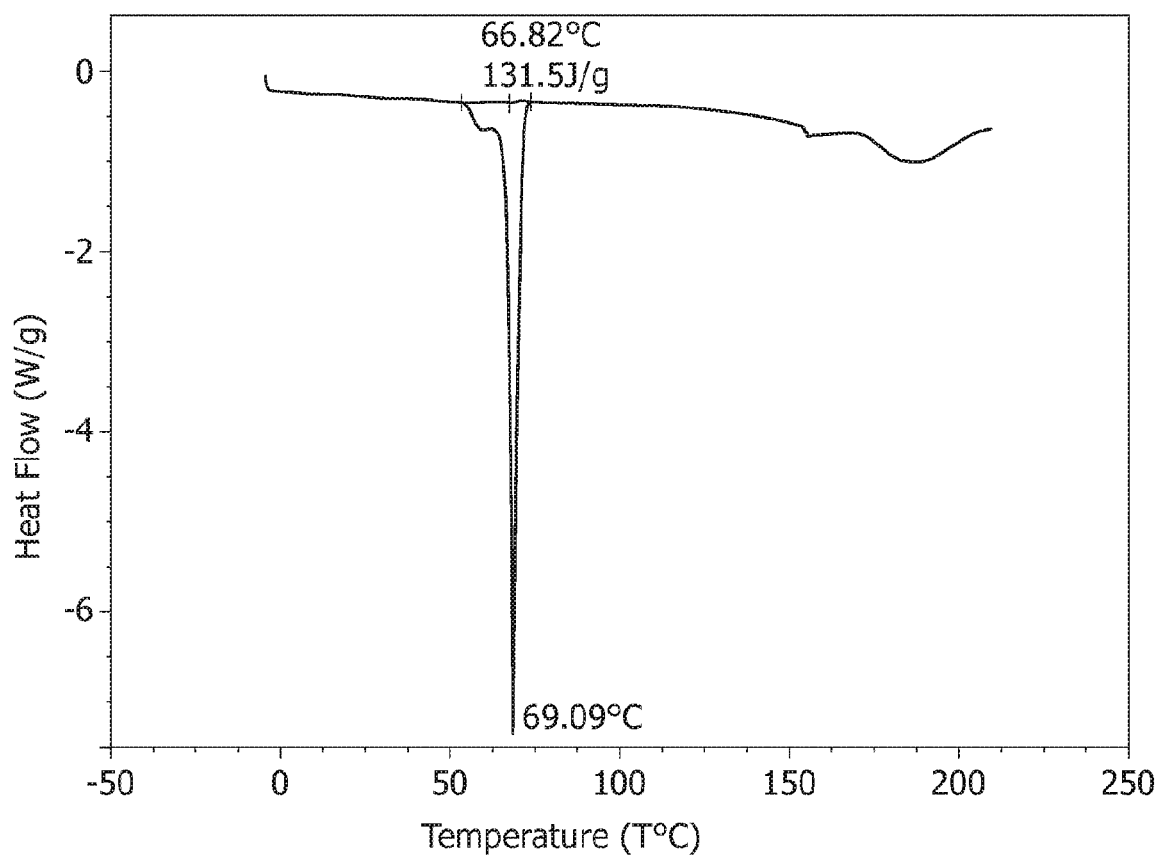
FIGS. 15 and 16 are diagrams related to thermograms.

By way of general guidance, and without this being considered, even only indirectly, in a limiting sense of the embodiments, the diagrams of FIGS. 1 to 3, as well as 15 and 16, exemplify:

FIG. 1: release profiles of a stent provided with recesses loaded with a first layer containing Sirolimus-Glyceryl behenate with a weight ratio of 45:55, and a second layer containing dexamethasone acetate-palmitic acid in a weight ratio of 65:35;

FIG. 2: release profiles of a stent provided with recesses loaded with a first layer containing dexamethasone acetate-palmitic acid and stearic acid with a weight ratio of 65:35, and a second layer containing Sirolimus-stearic acid in a weight ratio of 45:55;

FIG. 3: release profiles of a stent provided with recesses loaded with a first layer containing Sirolimus-stearic acid with a weight ratio of 45:55, and a second layer containing dexamethasone acetate-palmitic acid and stearic acid in a weight ratio of 65:35;

FIG. 15: a thermogram acquired by means of DSC Q2000 (TA instruments) of the formulation Sirolimus-stearic acid with a weight ratio of 45:55.

Figure 16:
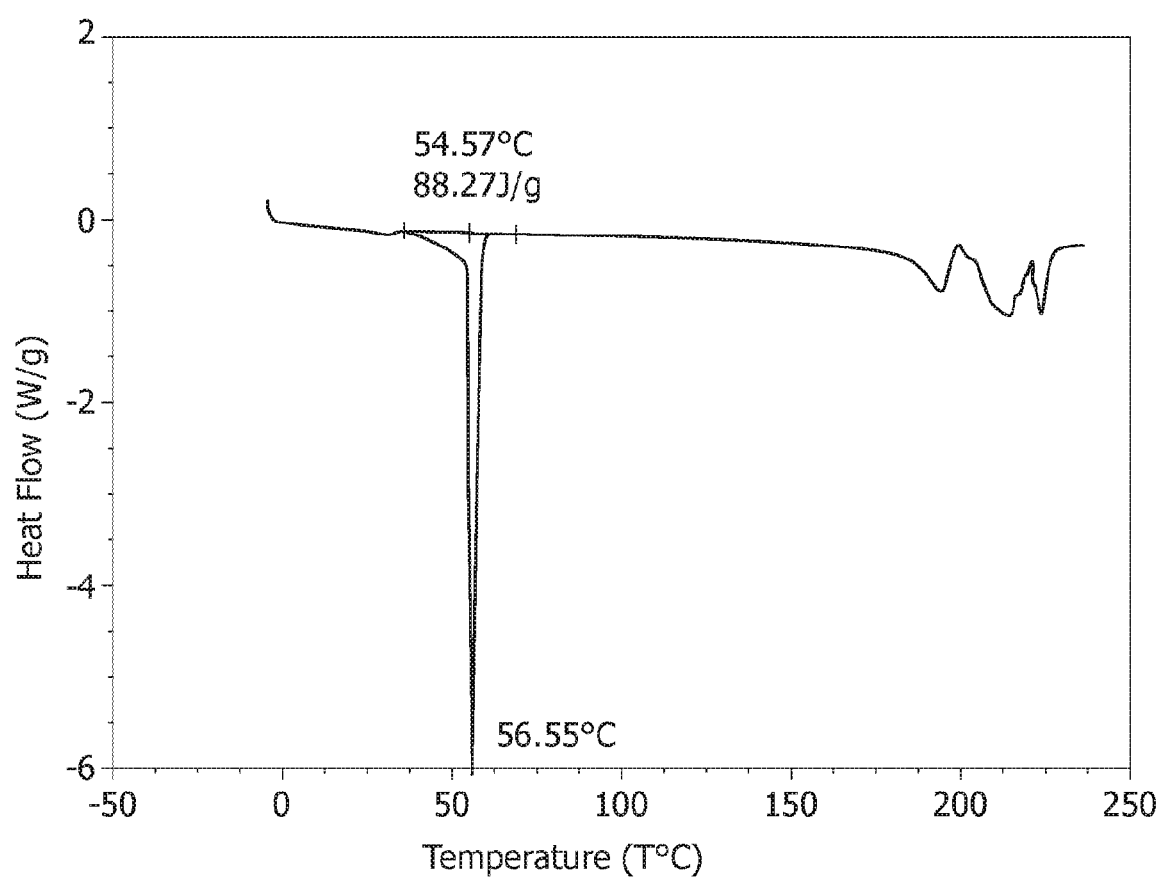
Figure 1:
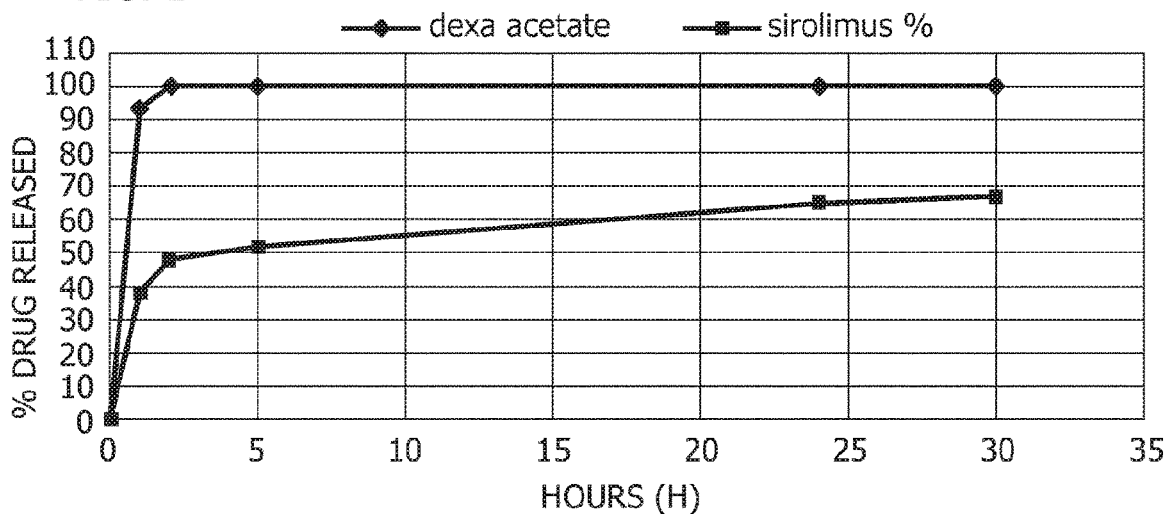
Figure 2:
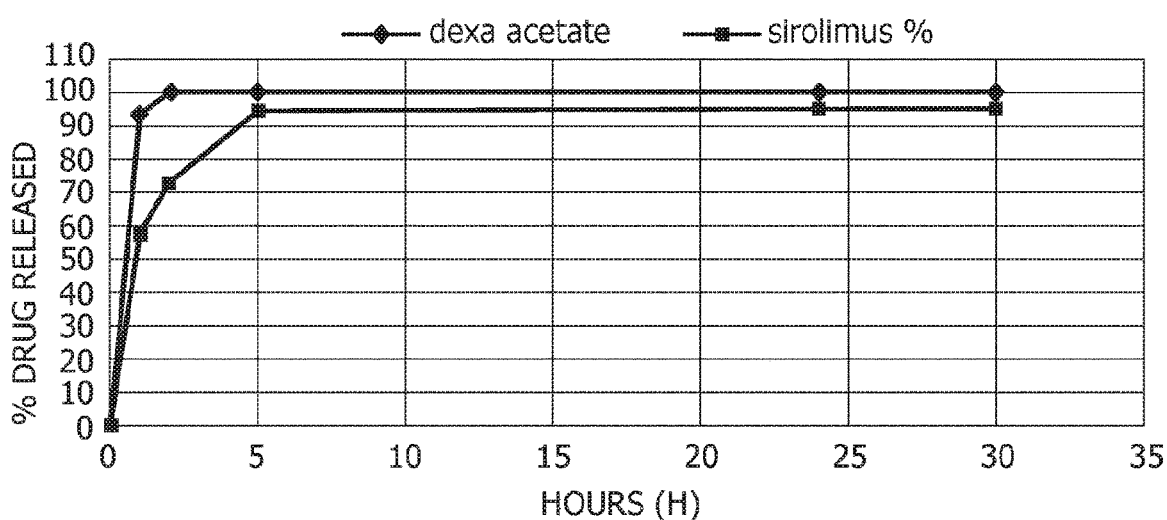
Figure 3:
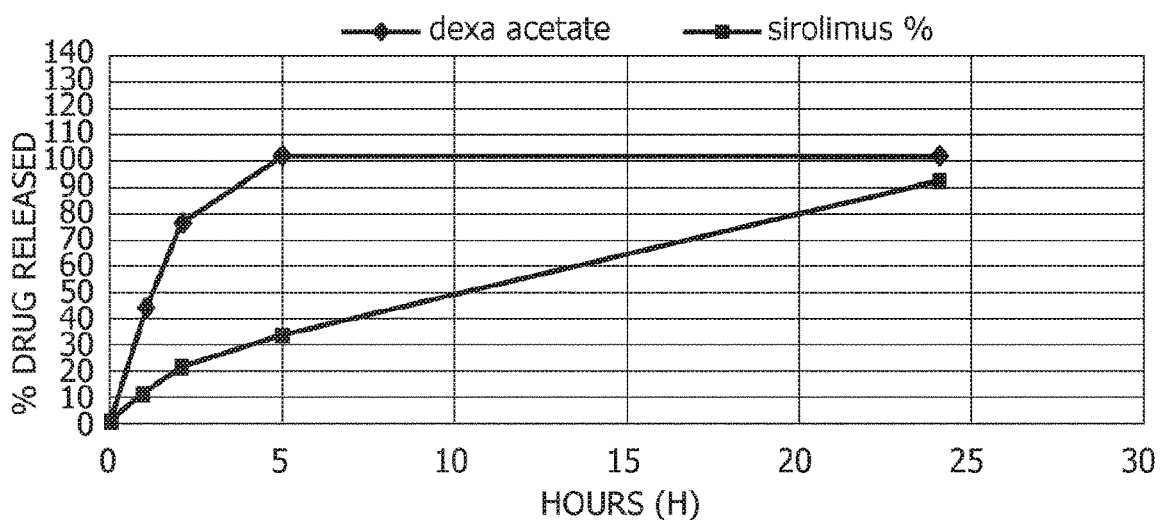
Figure 4:
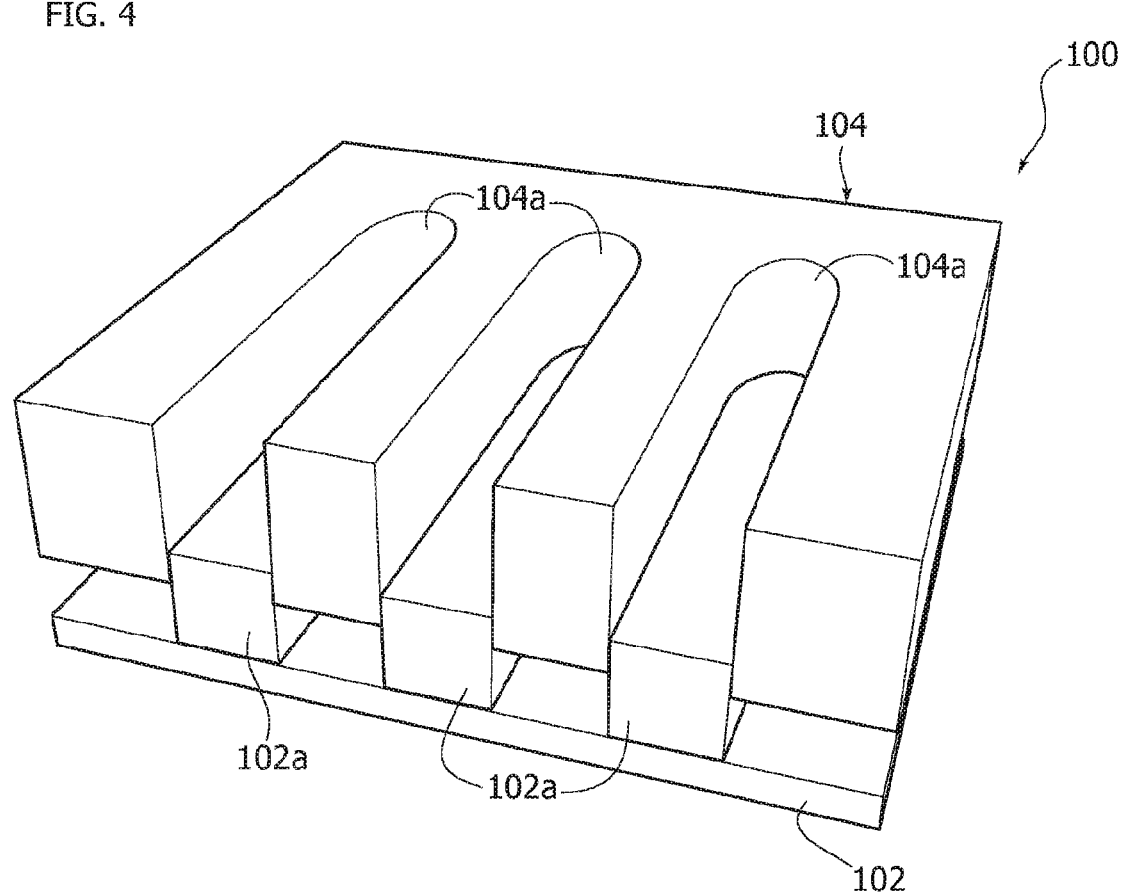
Figure 5:
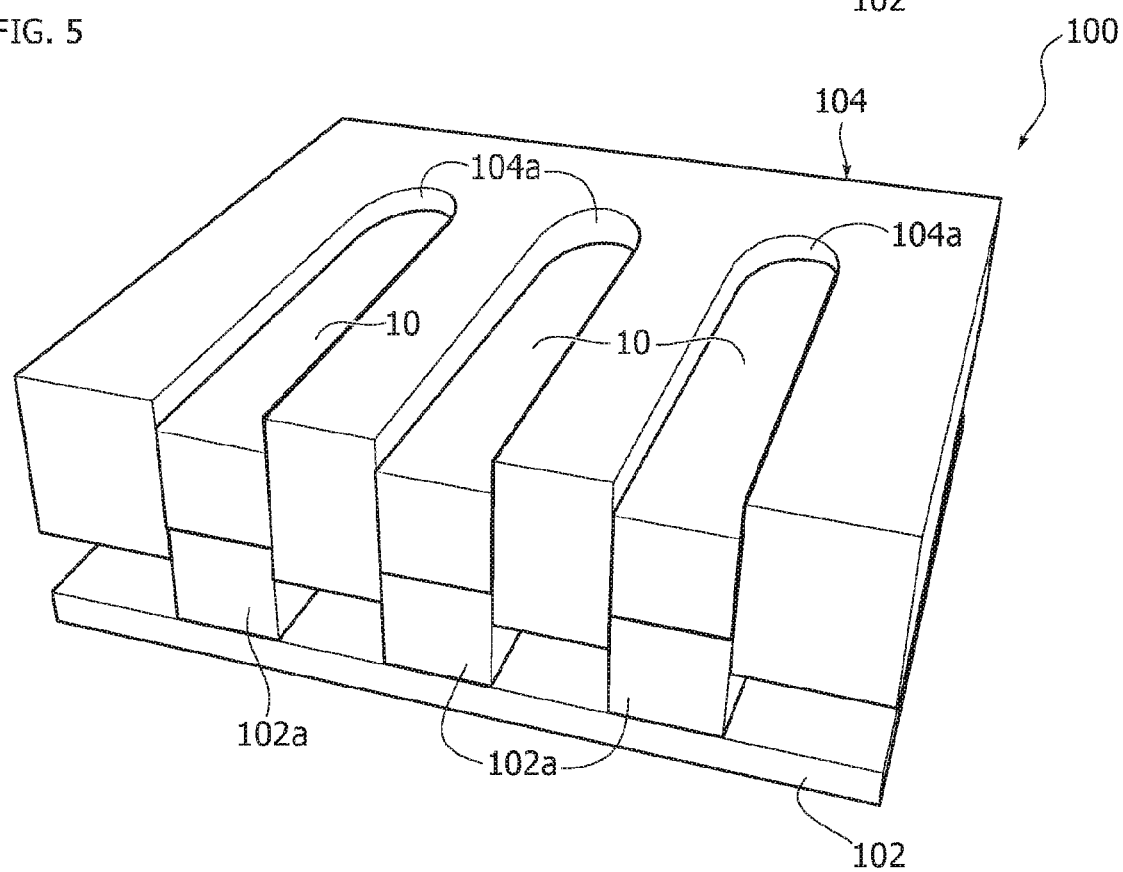
Figure 6:
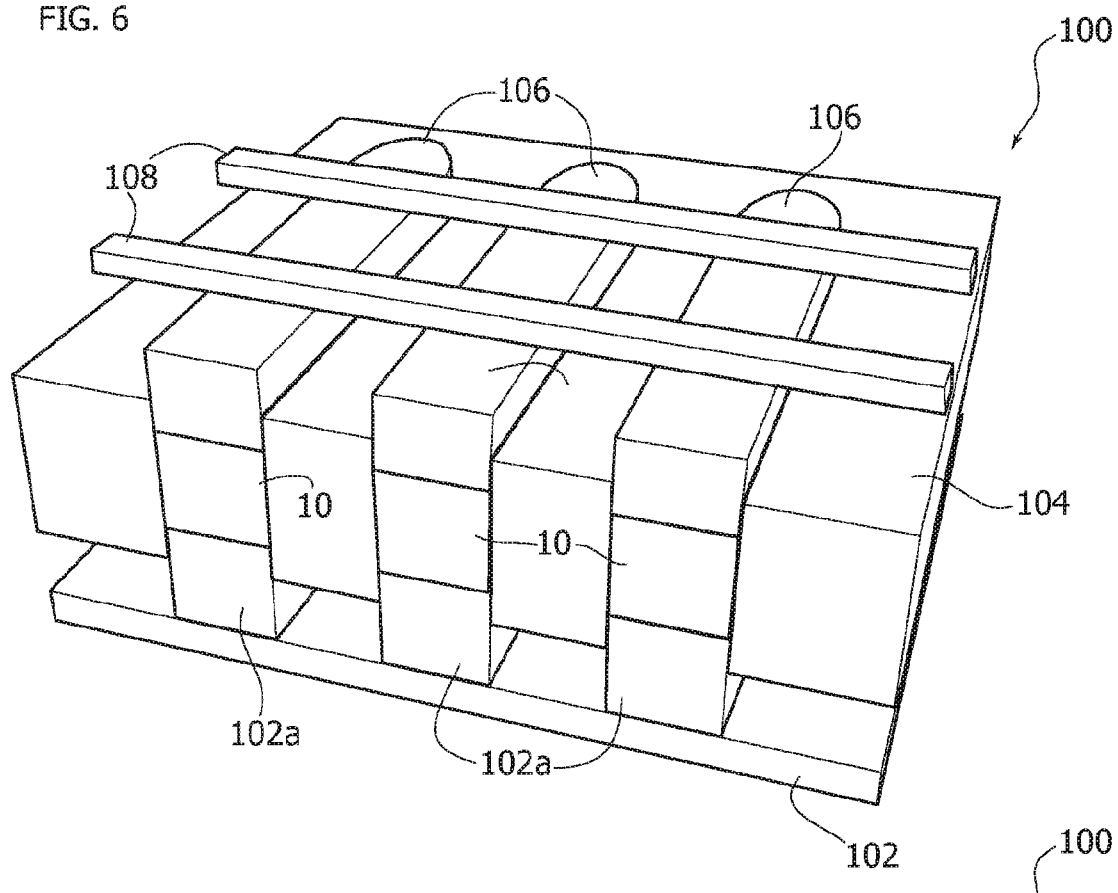
Figure 7:
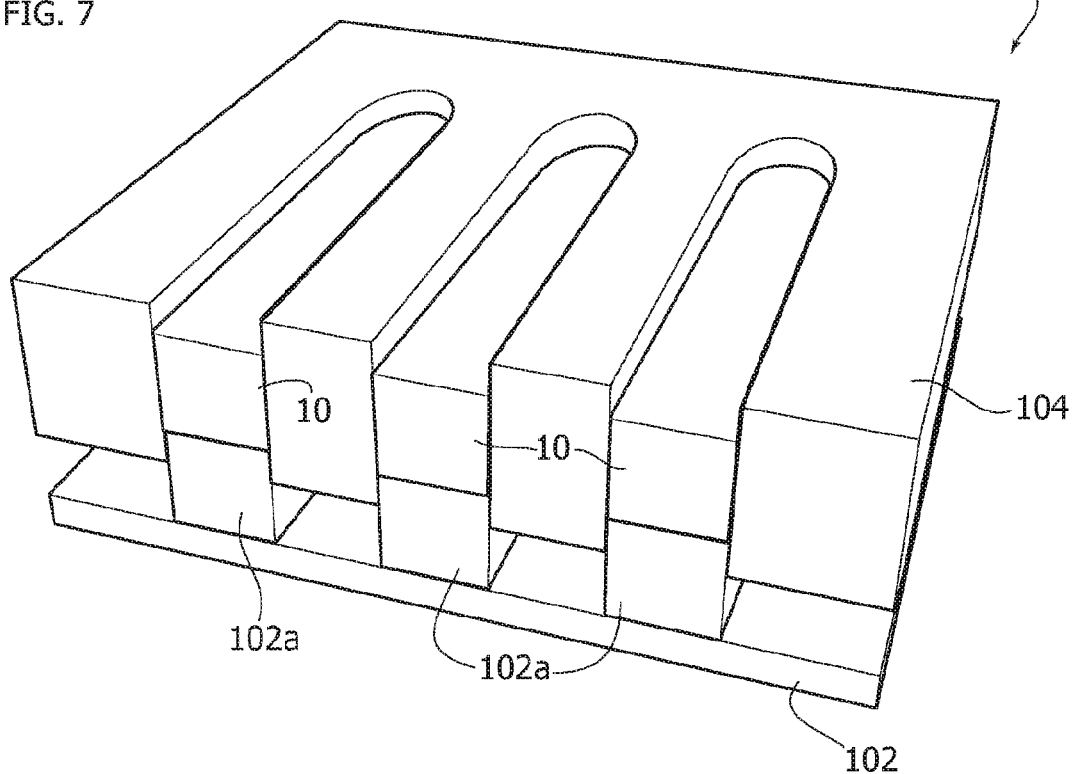
Figure 8:
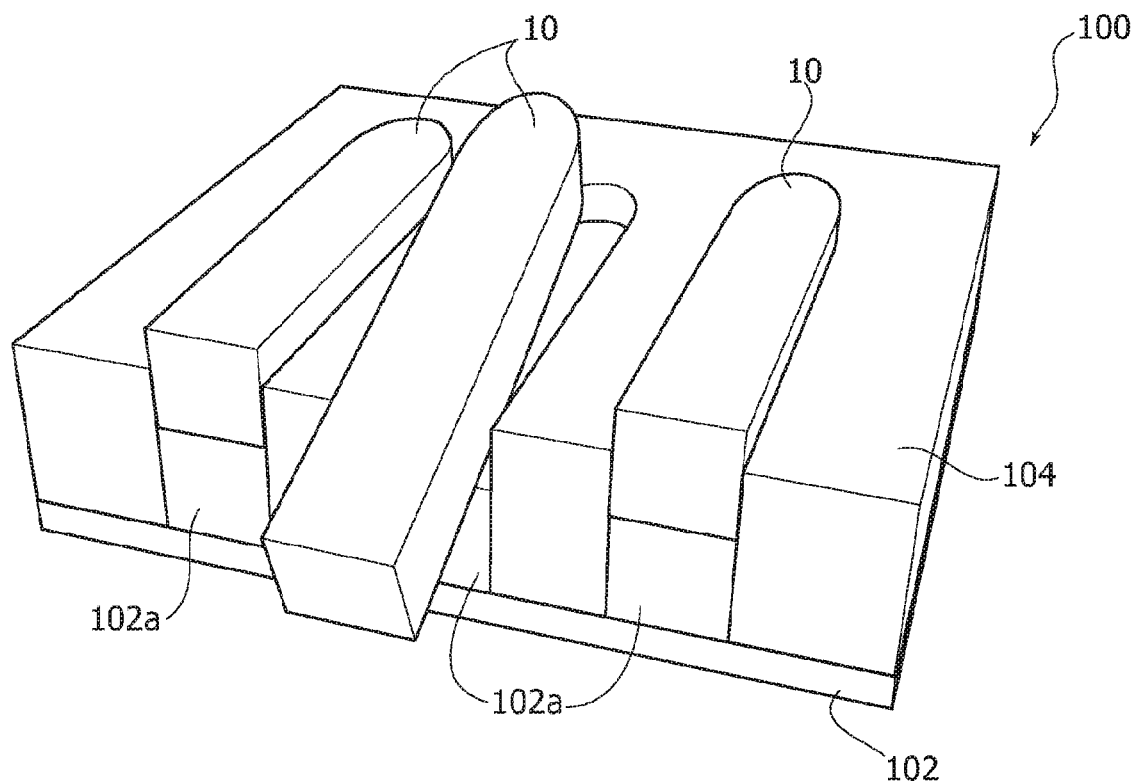
Figure 9:
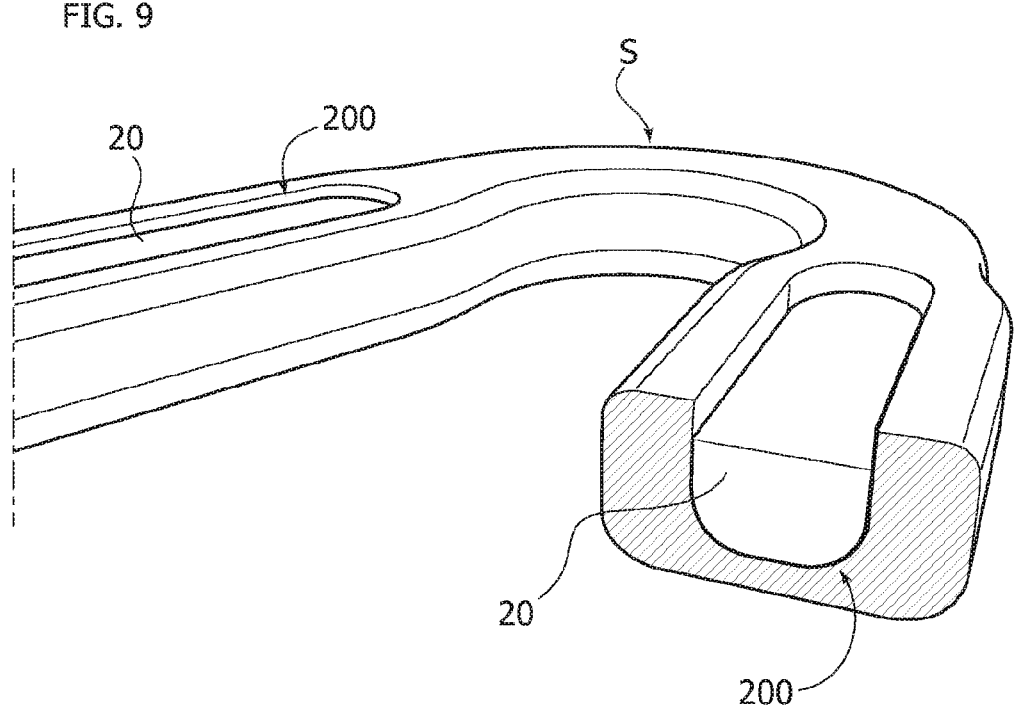
Figure 10:
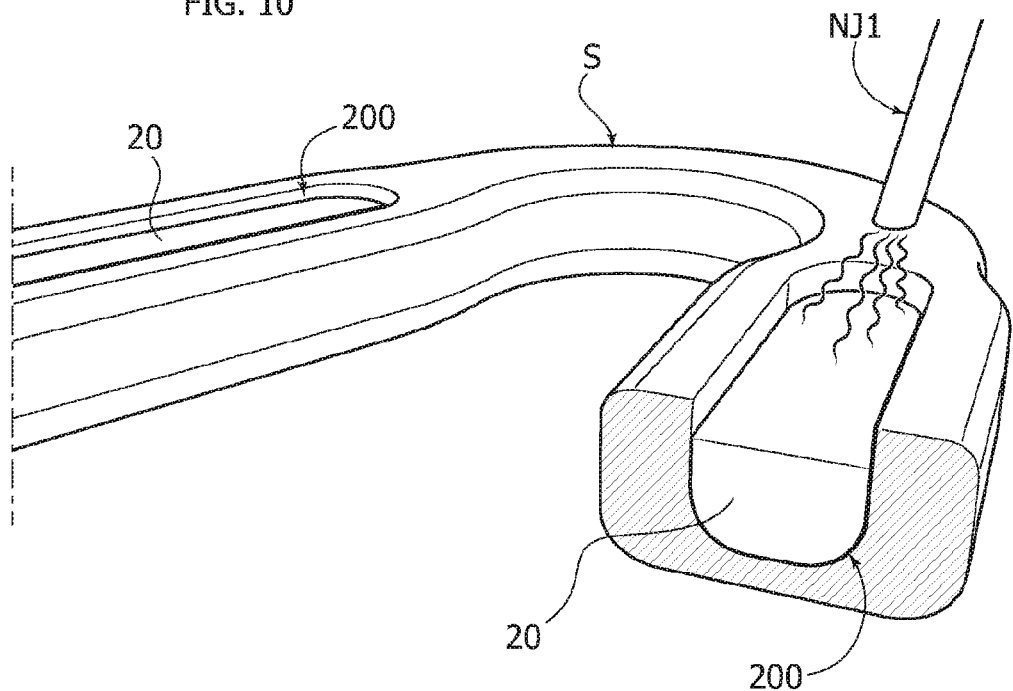
Figure 11:
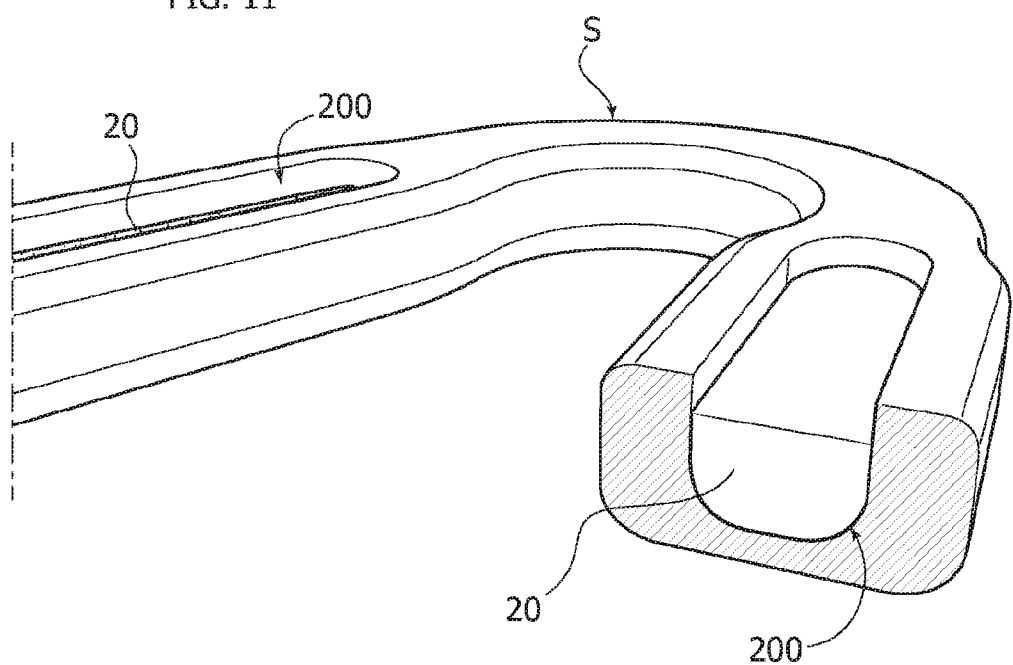
Figure 12:
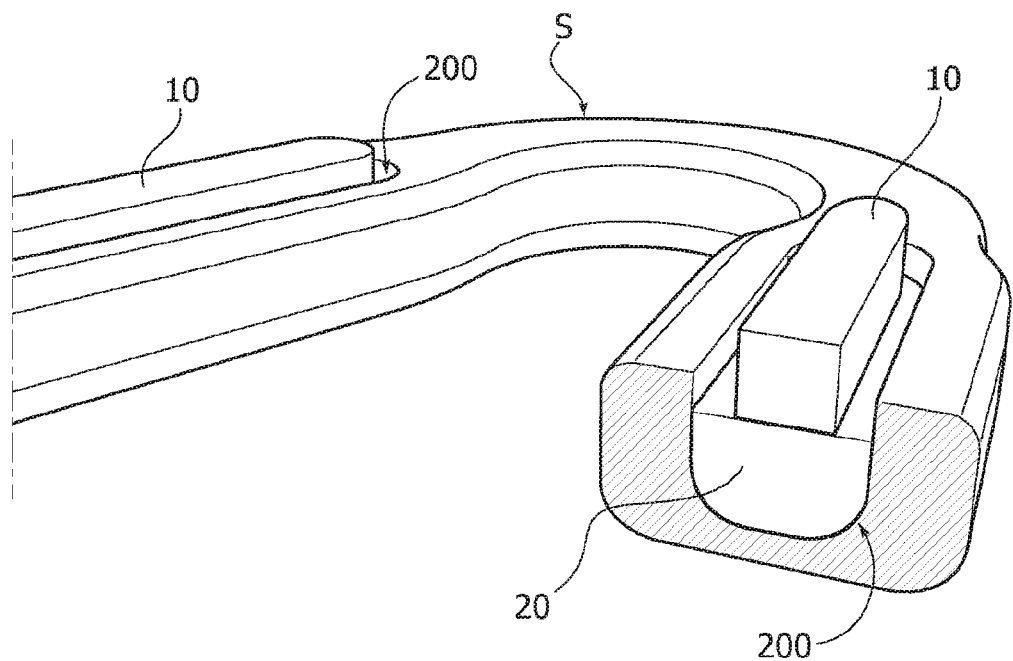
Figure 13:
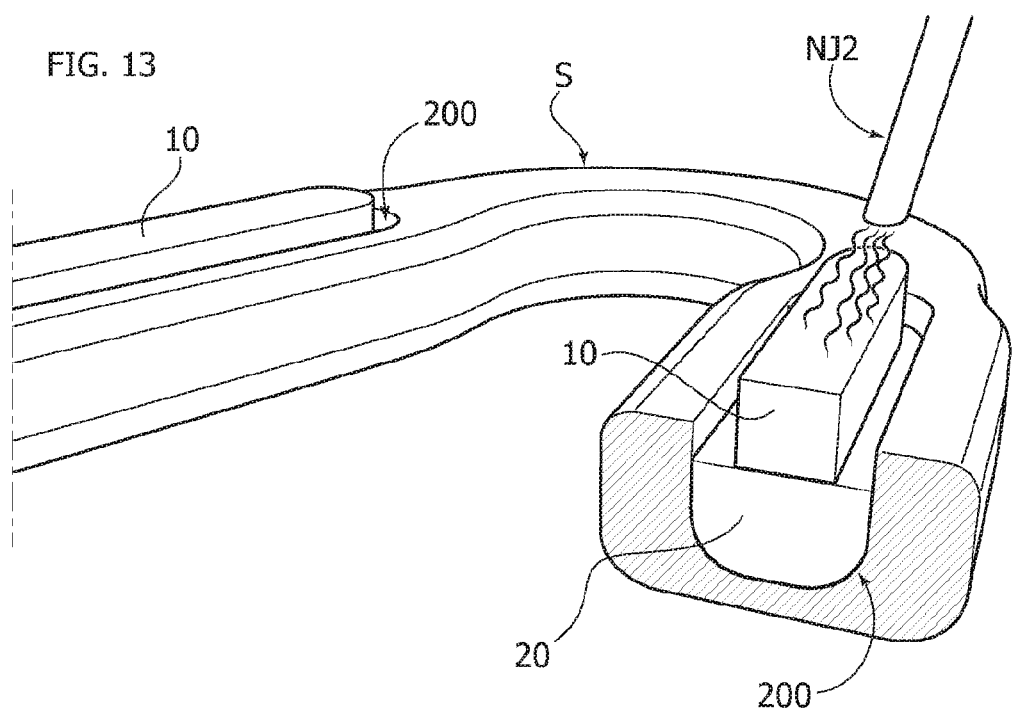
Figure 14:
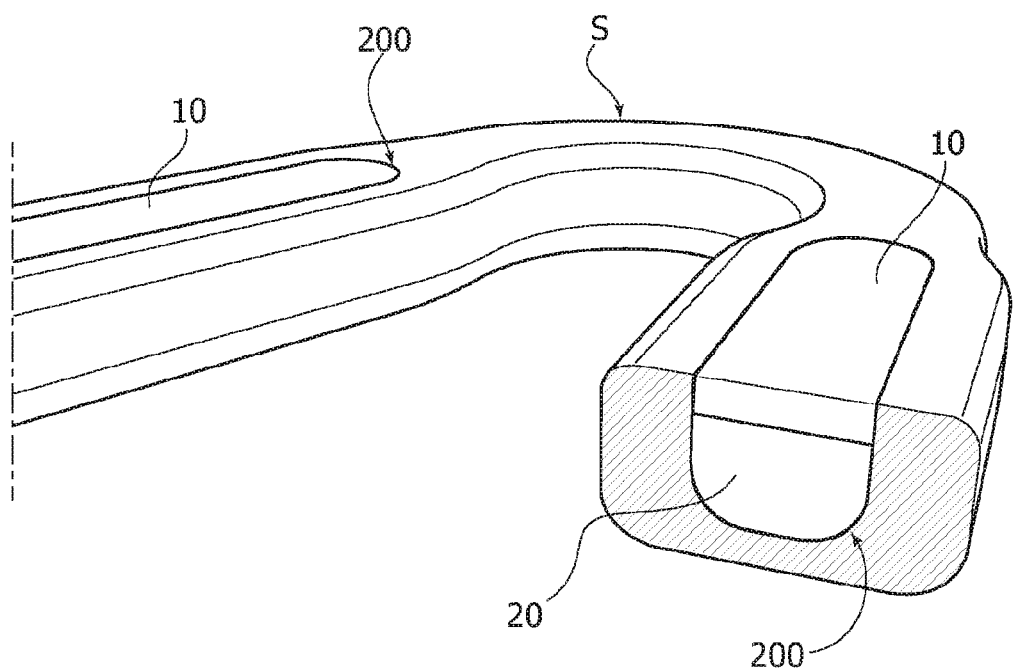
Figure 15:
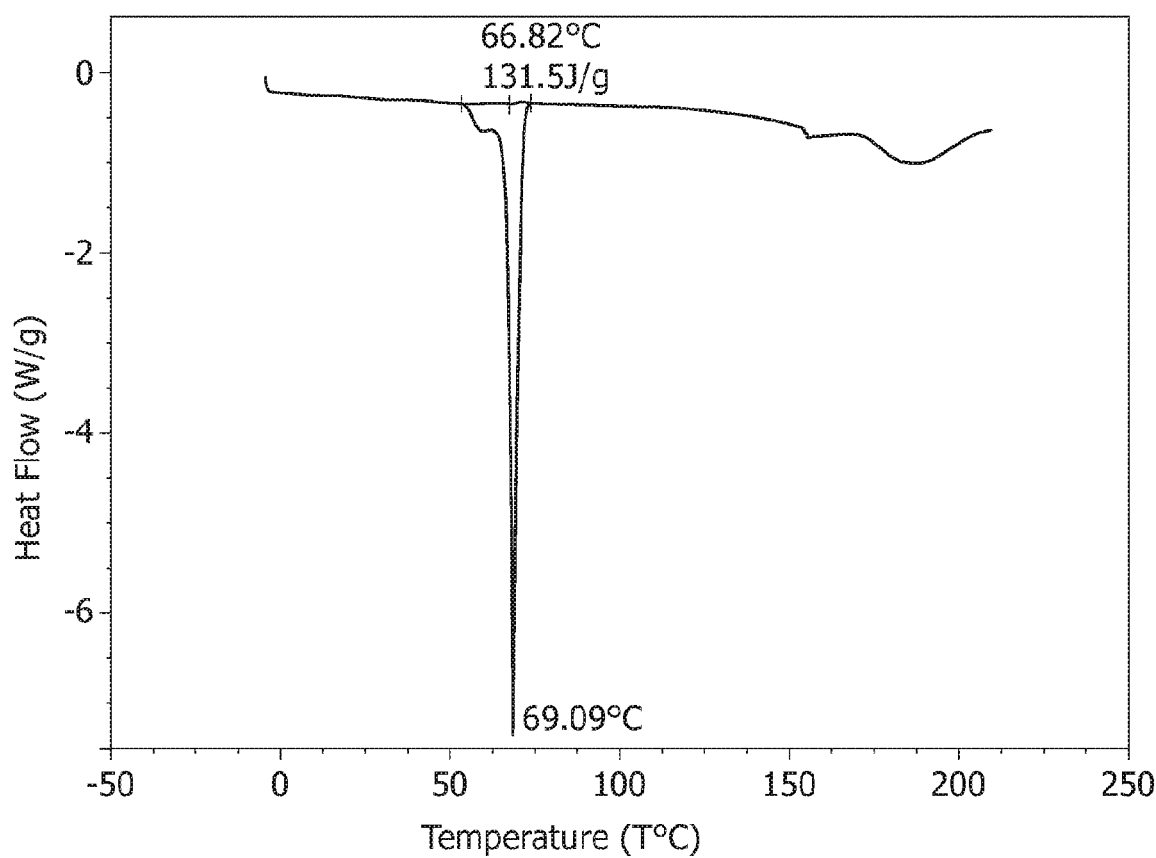
Figure 16:
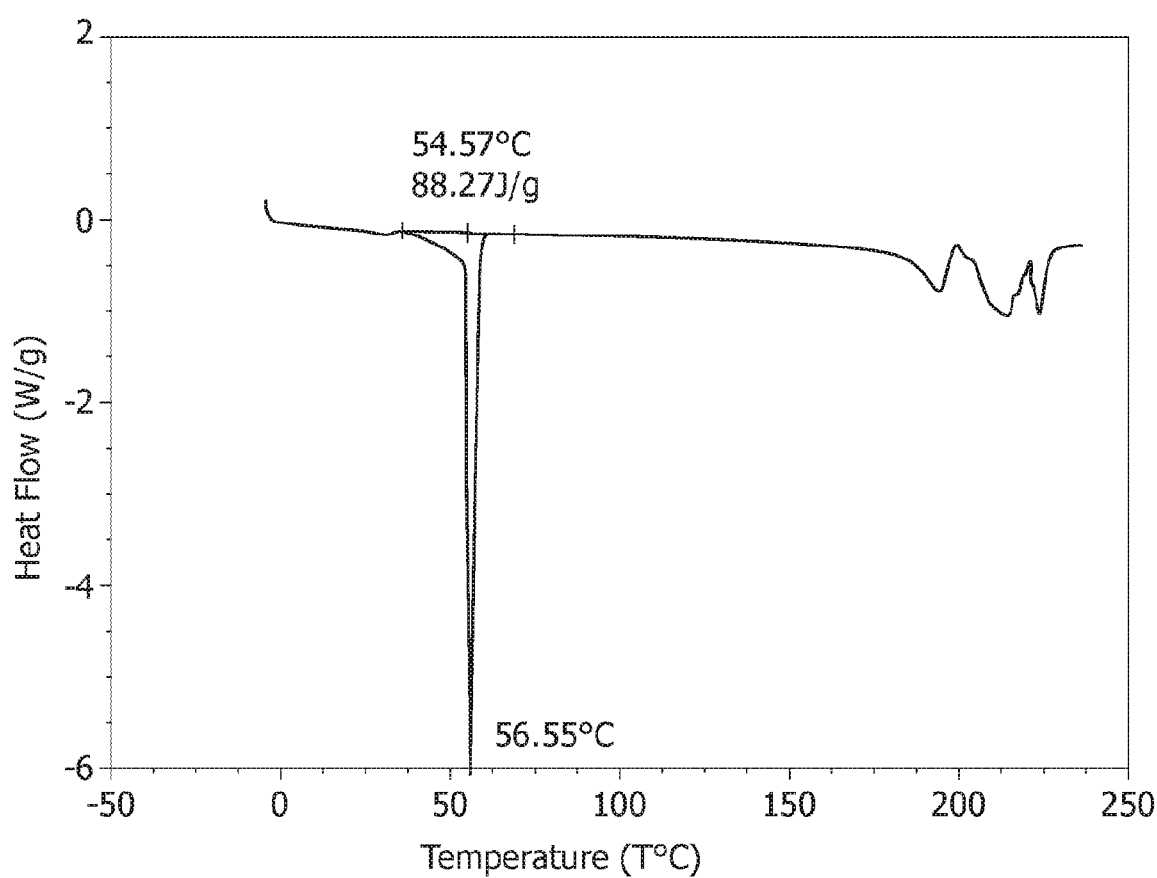

FIG. 16: a thermogram acquired by means of DSC Q2000 (TA instruments) of the formulation dexamethasone acetate-stearic/palmitic acid (50:50) with a weight ratio of 65:35.

Example 1—Comparative

First formulation: Sirolimus:Glyceryl behenate in a weight ratio 45:55

Second formulation: dexamethasone acetate:palmitic acid in a weight ratio 65:35

First layer: 110 mg of Glyceryl behenate (ester of fatty acid C22) was weighed into a Pyrex glass container, granulated in pentane with the aid of a pestle, to which 90 mg of Sirolimus was added.

The granulation was maintained under a suction fume hood for 0.5 hours. The obtained product is a white powder with the presence of very different particle sizes, so the powder was transferred to a mortar and ground for 2 minutes.

The first formulation was loaded—according to methods known in the art—within the recesses of a stent.

The loaded stent was subsequently subjected to a thermal stabilization method by exposing the stent to a stream of nitrogen heated to 70-78° C. for about 2 minutes followed by 3 minutes of cooling at room temperature so as to stabilize/fix the formulation within the recesses.

Second layer 130 mg of dexamethasone acetate was weighed into a Pyrex glass container, granulated in pentane with the aid of a pestle, to which 70 mg of palmitic acid was added.

The granulation was maintained under a suction fume hood for 1 hour. The obtained product is a white powder with the presence of very small particle sizes, so the powder was used as such.

The second formulation was loaded—according to methods known in the art—within the recesses of a stent preloaded with the first formulation.

The loaded stent was subsequently subjected to a thermal stabilization method by exposing the stent to a stream of nitrogen heated to 56-60° C. for about 2 minutes followed by 3 minutes of cooling at room temperature so as to stabilize/fix the second formulation within the recesses.

Example 2—Comparative

First formulation: dexamethasone acetate:stearic acid and palmitic acid (50:50) in a weight ratio 65:35

Second formulation Sirolimus:stearic acid in a weight ratio 45:55

First layer: 130 mg of dexamethasone acetate was weighed into a Pyrex glass container, granulated in pentane with the aid of a pestle, to which 70 mg of palmitic acid/stearic acid was added (50:50).

The granulation was maintained under a suction fume hood for 0.5 hours. The obtained product is a white powder with the presence of very small particle sizes, so the powder was used as such.

The first formulation was loaded—according to methods known in the art—within the recesses of the stent.

The loaded stent was subsequently subjected to a thermal stabilization method by exposing the stent to a stream of nitrogen heated to 50-58° C. for about 2 minutes followed by 3 minutes of cooling at room temperature so as to stabilize/fix the first formulation within the reservoirs.

Second layer 110 mg of stearic acid was weighed into a Pyrex glass container, granulated in pentane with the aid of a pestle, to which 90 mg of Sirolimus was added.

The granulation was maintained under a suction fume hood for 2 hours. The obtained product is a white powder with the presence of micrometric particle sizes, so the powder was transferred to a mortar and ground for 3 minutes.

The second formulation was loaded— according to methods known in the art— within the recesses of a stent preloaded with the first formulation.

The loaded stent was subsequently subjected to a thermal stabilization method by exposing the stent to a stream of nitrogen heated to 69-78° C. for about 2 minutes followed by 3 minutes of cooling at room temperature so as to stabilize/fix the second formulation within the reservoirs.

The heating was followed by 2 minutes of cooling at room temperature so as to stabilize/fix the first formulation within the reservoirs.

Example 3

First formulation: Sirolimus:stearic acid in a weight ratio 45:55

Second formulation: dexamethasone acetate:stearic acid and palmitic acid (50:50) in a weight ratio 65:35

First layer: 110 mg of stearic acid was weighed into a Pyrex glass container, granulated in pentane with the aid of a pestle, to which 90 mg of Sirolimus was added.

The granulation was kept under ultrapure nitrogen flow for 5 hours. The obtained product is a white powder with the presence of different particle sizes, so the powder was transferred to a mortar and ground for 3 minutes.

The first formulation was loaded— according to methods known in the art— within the recesses of a stent.

The loaded stent was subsequently subjected to a thermal stabilization method by heating the loaded stent to 68-78° C. for 2 minutes by passing it through a metal ring to which an electric current was applied.

The heating was followed by 2 minutes of cooling at room temperature so as to stabilize/fix the first formulation within the reservoirs Second layer 130 mg of dexamethasone acetate was weighed into a Pyrex glass container, granulated in pentane with the aid of a pestle, to which 70 mg of palmitic acid and stearic acid was added (50:50).

The granulation was maintained under a suction fume hood for 1 hour. The obtained product is a white powder with the presence of very small particle sizes, so the powder was used as such.

The second formulation was loaded— according to methods known in the art— within the recesses of a stent preloaded with the first formulation.

The loaded stent was subsequently subjected to a thermal stabilization method by exposing the loaded recesses to a stream of nitrogen heated to 56-60° C. for about 2 minutes followed by 3 minutes of cooling at room temperature so as to stabilize/fix the second formulation within the reservoirs.

Example 4. In Vitro Dissolution of the Active Principles Loaded onto Stents

The dissolution experiments were conducted by measuring the amount of drug released from the stent as a function of time.

Dissolution analyses were carried out in vitro in triplicate on stents produced as described in Examples 1 to 3.

The loaded stents were immersed in the dissolution medium in amber glass vials.

The operating conditions used are:
Dissolution medium: acetate buffer pH 4.8 with 0.08% SDS (sodium dodecyl sulfate);
Rocking waterbath thermostated at 37° C. with 80 oscillations per minute;
Complete replacement of the dissolution medium at each sampling (for each time point);
Filtration of the samples and analysis by UV spectroscopy (Perkin Elmer Lambda 35 spectrophotometer);
analytical method for evaluating Sirolimus:
Range of wavelengths: 450 to 200 nm
Bandwidth: 1 nm
Scanning speed: 480 nm/min
λmax: 279-280 nm
Maximum characteristic absorption: 268-269, 279-280, 291-292 nm
Quartz cuvette: 1.4 mL, 10 mm optical path;
analytical method for evaluating dexamethasone acetate:
Range of wavelengths: 450 to 200 nm
Bandwidth: 1 nm
Scanning speed: 480 nm/min
Maximum characteristic absorption: 241 nm
Quartz cuvette: 1.4 mL, 10 mm optical path;
construction of cumulative release curves over time (sum of the quantities released at various time points so as to calculate the % of release compared to the initial dose loaded on the stent).

At the end of the dissolution experiments, the stent reservoirs were observed under a microscope at a magnification of ×40 and were completely empty.

The dissolution profiles of the stents produced according to that which is indicated in examples 1 to 3 are illustrated graphically in FIGS. 1 to 3, respectively. The quantities by weight of the active principles released from the stents of Examples 1 to 3 are also provided in Tables 1 to 3, respectively.

TABLE 1

| | Dexamethasone acetate | | | Sirolimus | | |
|---|---|---|---|---|---|---|
| time (hours) | μg released | cumulative sum over time | % theoretical release | μg released | cumulative sum over time | % theoretical release |
| 0 | 0 | 0 | 0 | 0 | 0 | 0 |
| 1 | 41 | 41 | 93 | 15 | 15 | 38 |
| 2 | 3 | 44 | 100 | 4 | 19 | 47 |
| 5 | 0 | 44 | 100 | 2 | 21 | 52 |
| 24 | 0 | 44 | 100 | 6 | 27 | 65 |
| 30 | 0 | 44 | 100 | 2 | 29 | 67 |

TABLE 2

| | Dexamethasone acetate | | | Sirolimus | | |
|---|---|---|---|---|---|---|
| time (hours) | μg released | cumulative sum over time | % theoretical release | μg released | cumulative sum over time | % theoretical release |
| 0 | 0 | 0 | 0 | 0 | 0 | 0 |
| 1 | 122 | 122 | 93 | 39 | 39 | 58 |
| 2 | 25 | 147 | 100 | 11 | 50 | 73 |
| 5 | 10 | 157 | 100 | 14 | 64 | 94 |
| 24 | 0 | 157 | 100 | 1 | 65 | 96 |
| 30 | 0 | 157 | 100 | 0 | 65 | 96 |

TABLE 3

| | Dexamethasone acetate | | | Sirolimus | | |
|---|---|---|---|---|---|---|
| time (hours) | μg released | cumulative sum over time | % theoretical release | μg released | cumulative sum over time | % theoretical release |
| 0 | 0 | 0 | 0 | 0 | 0 | 0 |
| 1 | 11 | 11 | 42 | 6 | 6 | 13 |
| 2 | 10 | 21 | 78 | 4 | 10 | 22 |
| 5 | 23 | 44 | 100 | 3.5 | 15.5 | 34 |
| 24 | 0 | 44 | 100 | 27 | 42.5 | 94 |

It is evident that the selection of the nature of the excipients used for producing the two formulations to be loaded onto the stent strongly affects the dissolution profiles.

In particular, it can be seen from FIG. 1 that the use of a fatty acid ester (glyceryl behenate) for the formulation of the sirolimus contained in the first layer does not allow a complete release of the sirolimus present on the stent, which reaches a percentage of dissolution of about 67%.

FIG. 2 demonstrates that the reversal of the physical properties of the excipients for producing the first and the second layers (that is, using excipients—albeit based on fatty acids—having a higher melting temperature for the second layer and a lower melting temperature for the first layer) does not allow the required release to be obtained. Both active principles are released with fast kinetics and a complete release in the first few hours of testing.

FIG. 3 illustrates a dissolution profile of a stent produced according to the present description, that is, using a first excipient based on a fatty acid having a melting temperature between 69 and 80° C. and a mixture of two fatty acids in which the mixture has a melting temperature between 50 and 65° C. As can be seen clearly from FIG. 3, the stent releases the second active principle loaded onto the second layer (the outermost one) during the first few hours, and only subsequently releases the first active principle loaded onto the first layer (the innermost one) for a longer period.

Example 5. "Pick and Place" Load Method of Micro-Tablets of the Formulation to Stratify In one or more embodiments, the stents can have reservoirs on their outer surface, in the form of recesses, able to contain a first and a second active principle loaded within the recesses in a layered configuration using respective first and second excipients, selected from linear or branched saturated fatty acids, having different melting temperatures from each other.

In one or more embodiments, the outermost layer can be produced with the deposition of (micro)tablets obtained by compression of the powder of the second formulation within the recesses previously loaded with the first powder formulation.

The compression into microtablets allows maximization of loading avoiding empty spaces and producing a more uniform layer once fixed thermally due to being devoid of air.

Figure 4:
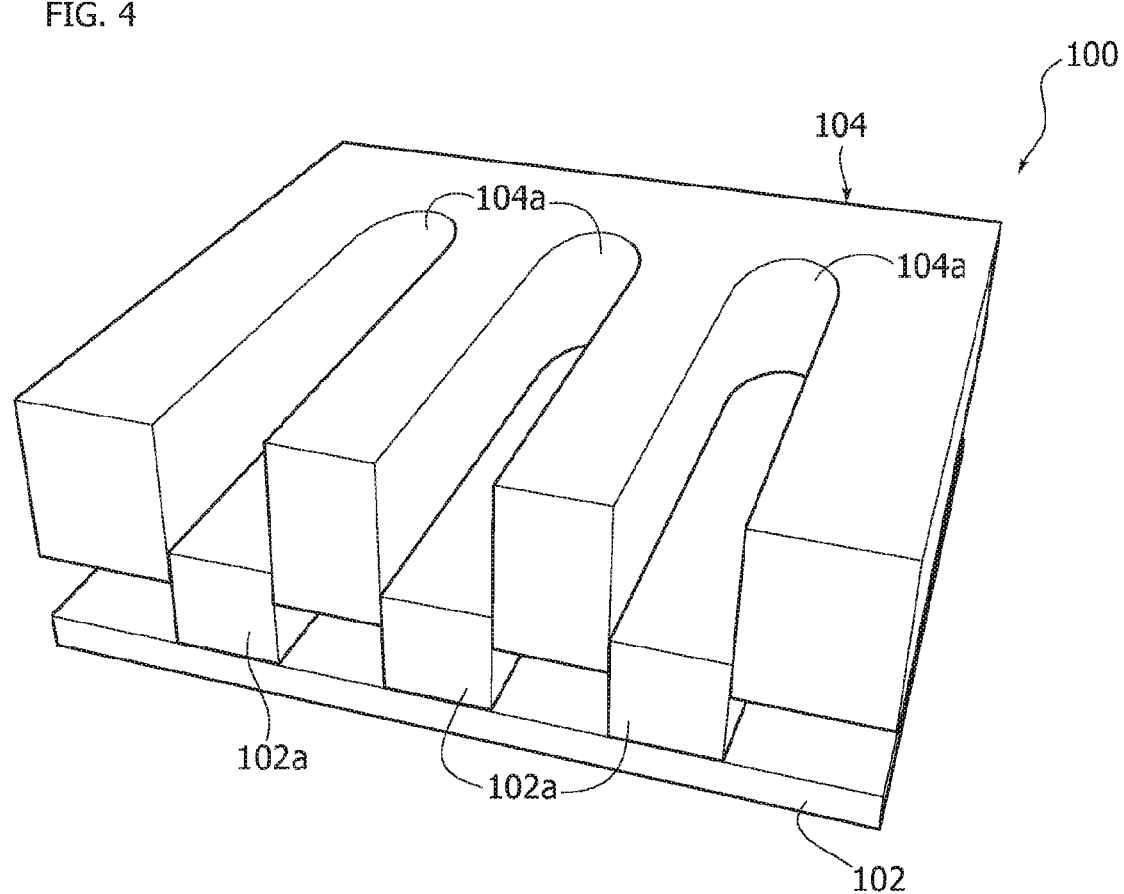
FIGS. 4 to 8 are exemplary of the production of tablets of active substance loadable in recesses of a stent.

For example, FIG. 4 illustrates, cross-sectioned in an ideal median plane, the possible structure of a (micro) tableting machine 100 for producing microtablets of a formulation 10 (containing e.g. an anti-inflammatory drug) to be placed onto the outermost layer of the recess of the stent In one or more embodiments, the tableting machine 100 can be made of a material such as AISI steel and comprising a base plate 102 provided with raised parts 102a.

Figure 5:
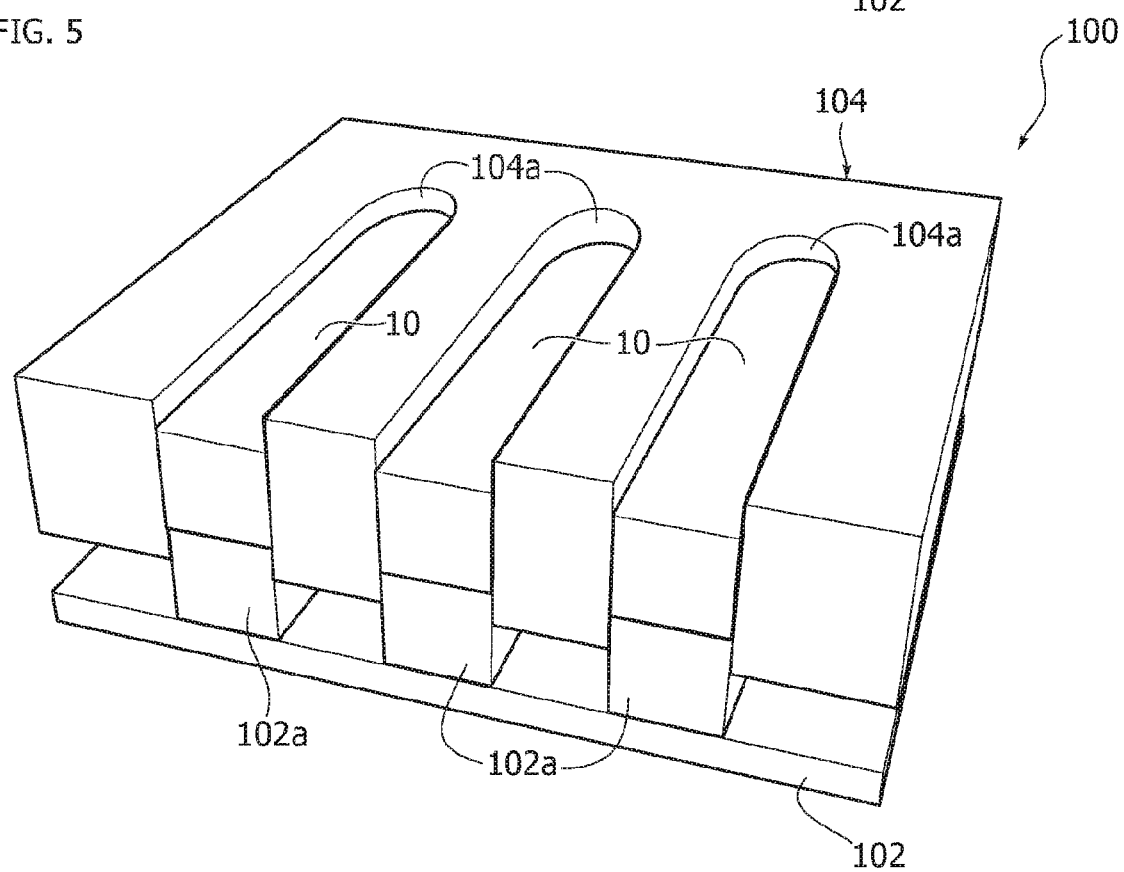

Thus, as can be seen e.g. in FIG. 5, an additional plate 104 can be fitted on the plate 102, provided with slotted openings 104a suitable for fitting onto the raised parts 102a so as to form, at the raised parts 102a, respective mold cavities in which the formulation 10 in powder-form can be loaded.

Figure 6:
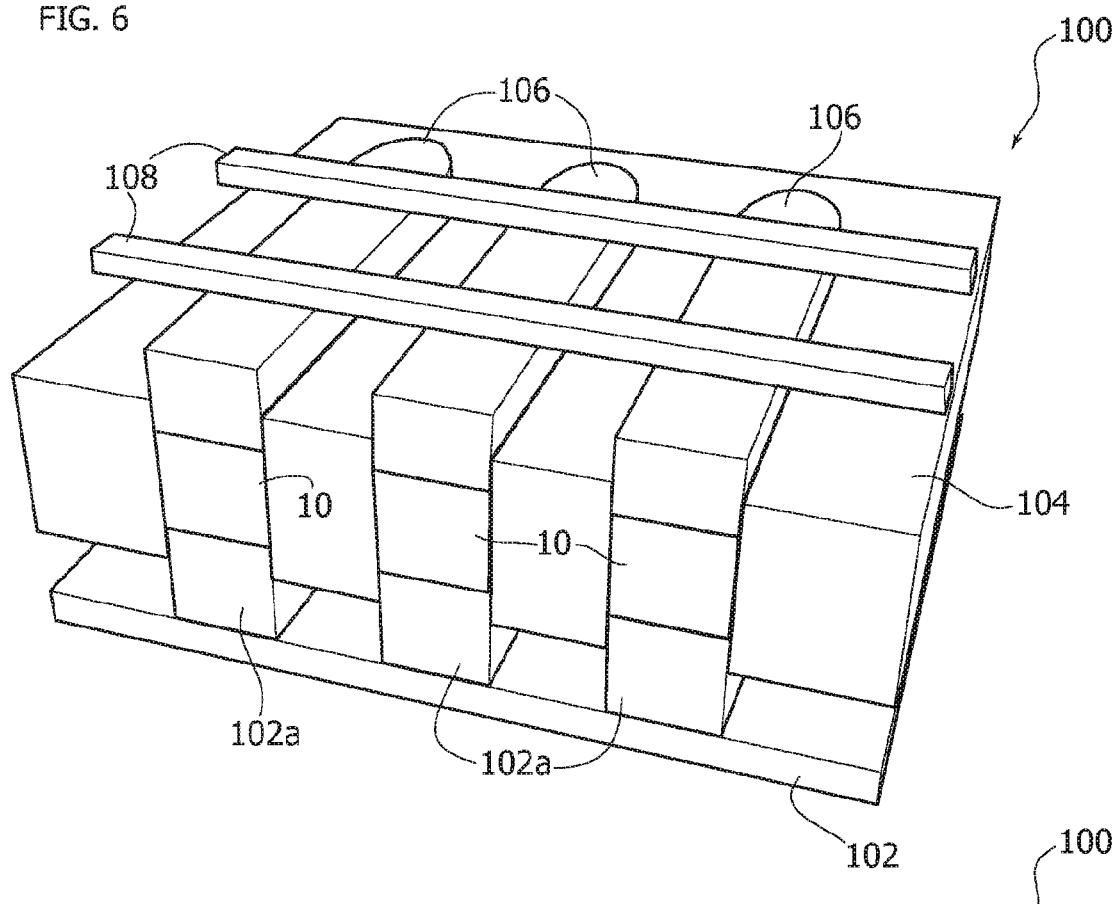

Above the formulation 10, in the aforesaid mold cavities, dowel pressers 106 can be inserted, able to act (e.g. under the action of thrust means represented for simplicity in FIG. 6 in the form of simple compression rods 108) as pressing pistons so as to compress the powder formulation 10 previously introduced into the mold.

The plates 102 and 104 can be positioned at different relative heights so as to be able to modulate the thickness of the (micro)tablets, and therefore the dosage of the powder of the formulation 10.

In one or more embodiments, by means of the use of the tableting machine 100, it is possible to produce solid microtablets by means of a moderate pressure and not influential on the physical structure of the formulation (maintaining the crystalline state of the mixture of excipients and anti-inflammatory drug).

Figure 7:
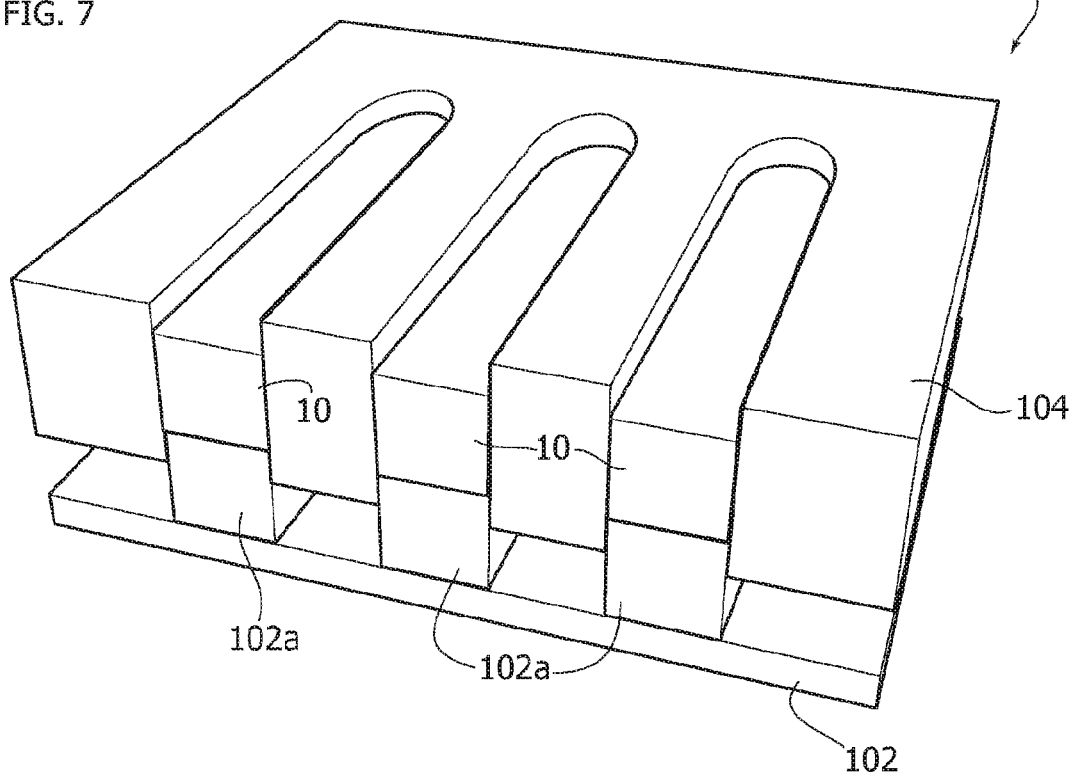
Figure 8:
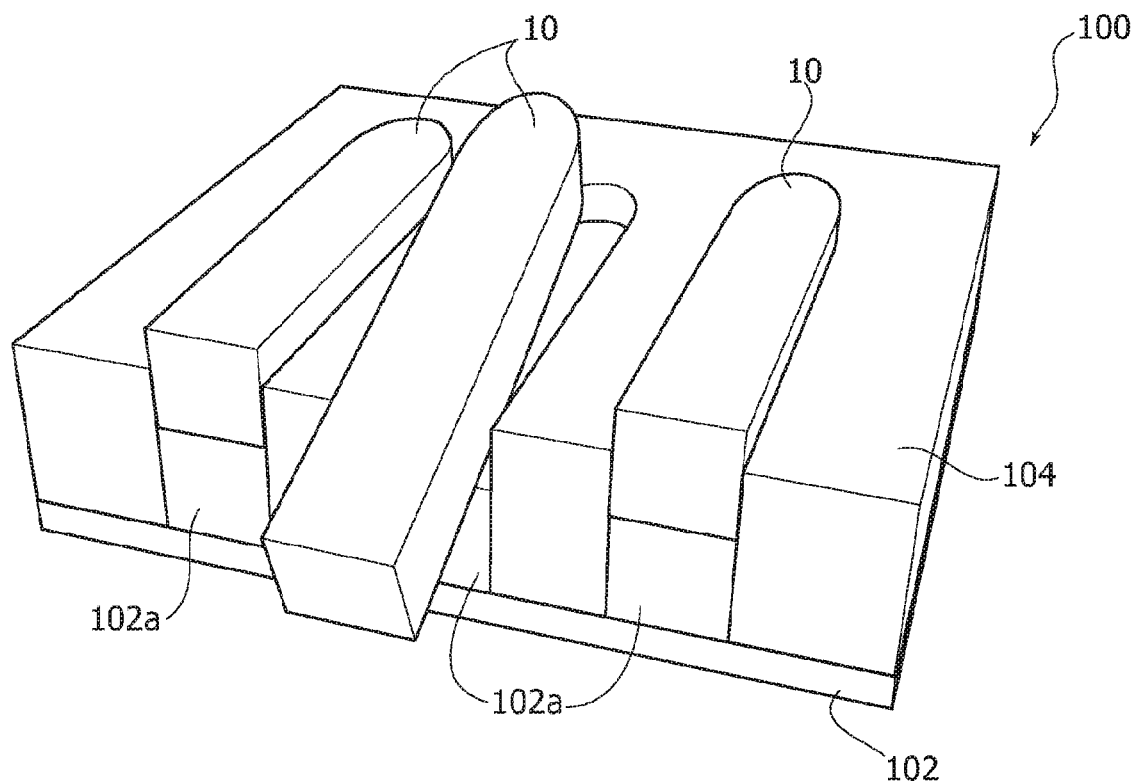
Figure 9:
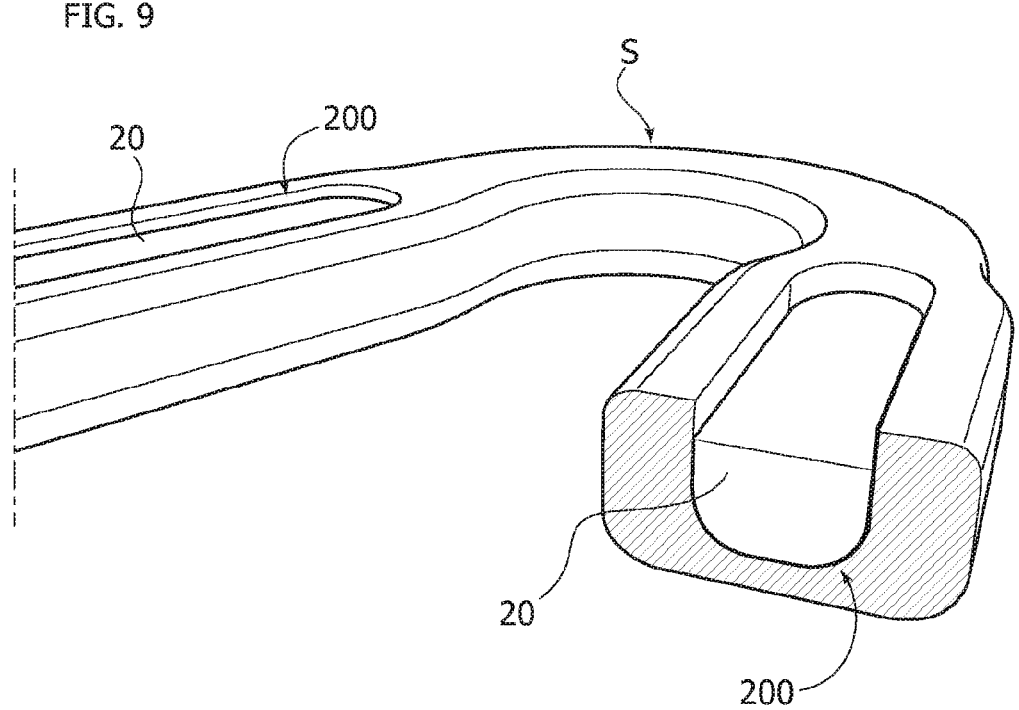
FIGS. 9 to 14 are exemplary of the loading of active substances in the recess of a stent.

Once the microtablets have been produced (FIG. 7), they can be expelled (FIG. 8) e.g. with a micropiston system and positioned in the recesses of a stent, e.g. with a "pick and place" system.

FIGS. 9 to 14 exemplify the possible positioning of tablets of the type exemplified above into recesses 200 provided (in a manner known per se, e.g. by means of laser beam) on the surface of a stent S.

In one or more embodiments (see FIG. 9), the recesses 200 may have been at least partially loaded (also in this case in a manner known per se) with an additional formulation 20, e.g. powder, suitable for containing an anti-proliferative drug (e.g. a mixture of excipients and an anti-proliferative drug).

Figure 10:
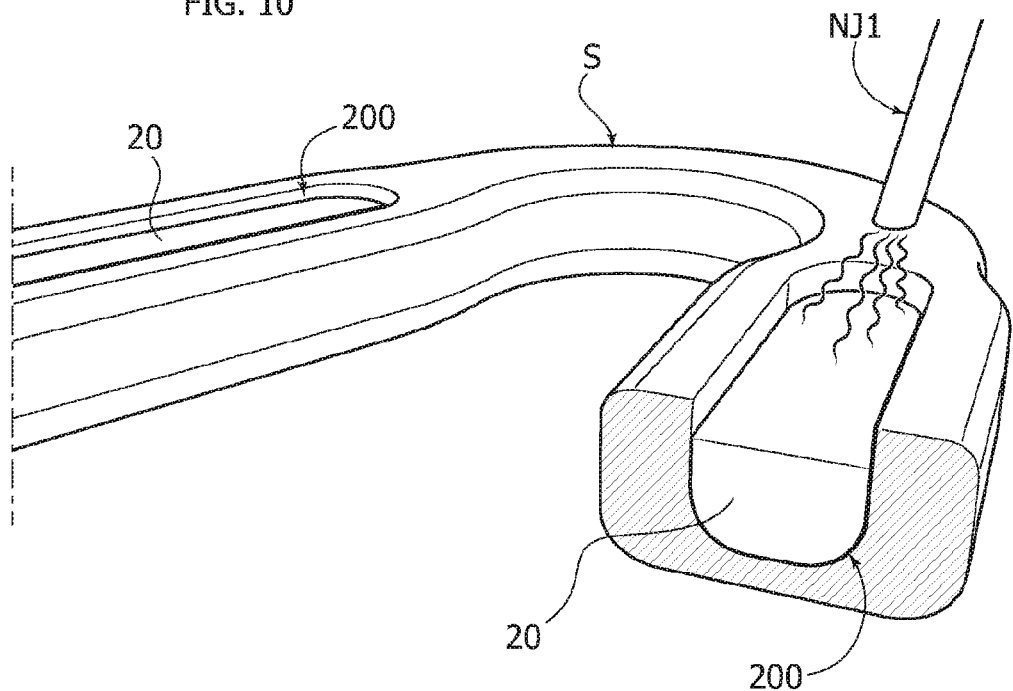
Figure 11:
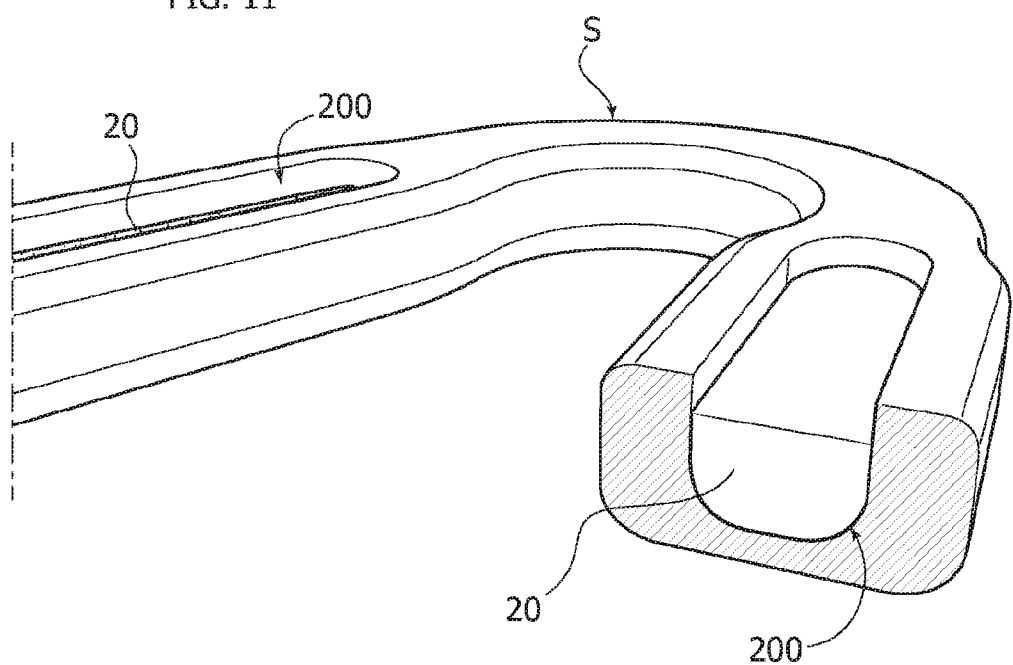
Figure 12:
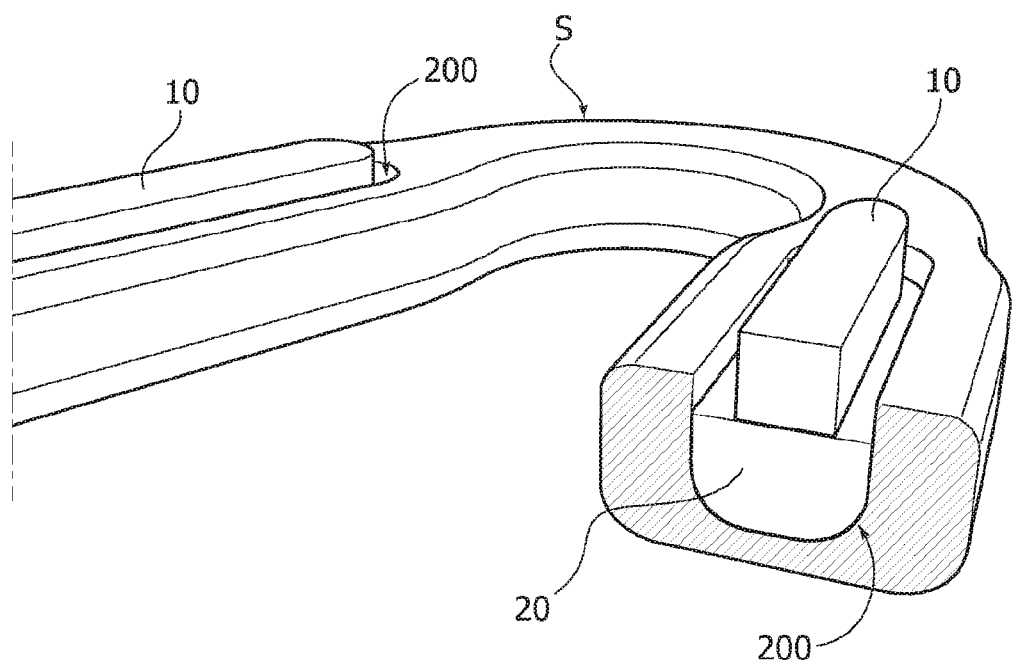
Figure 13:
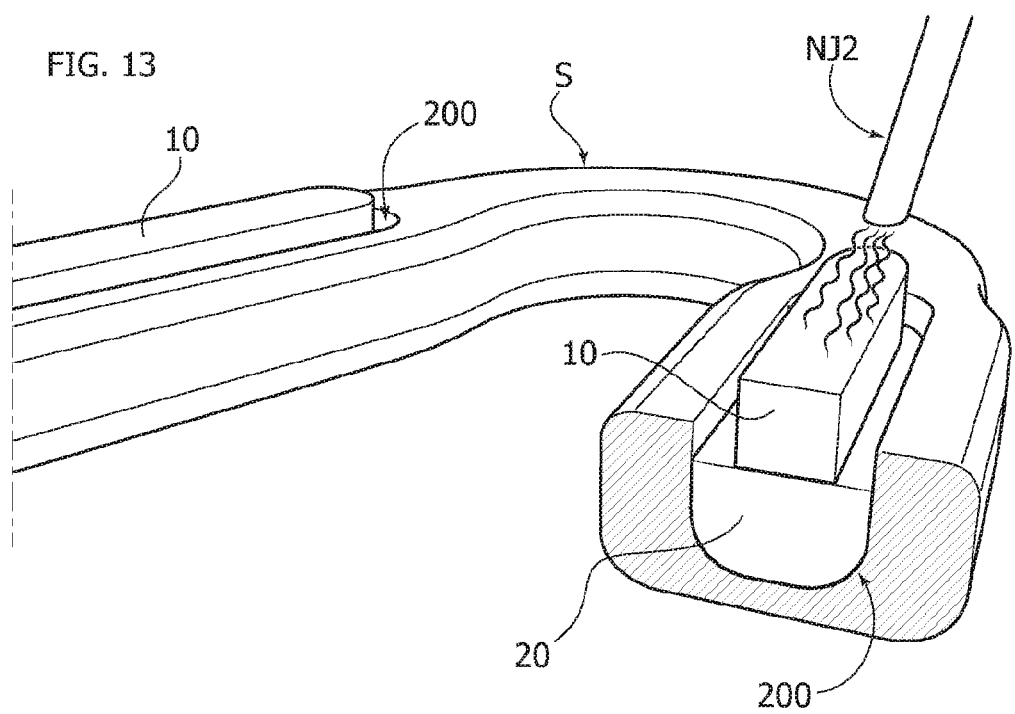
Figure 14:
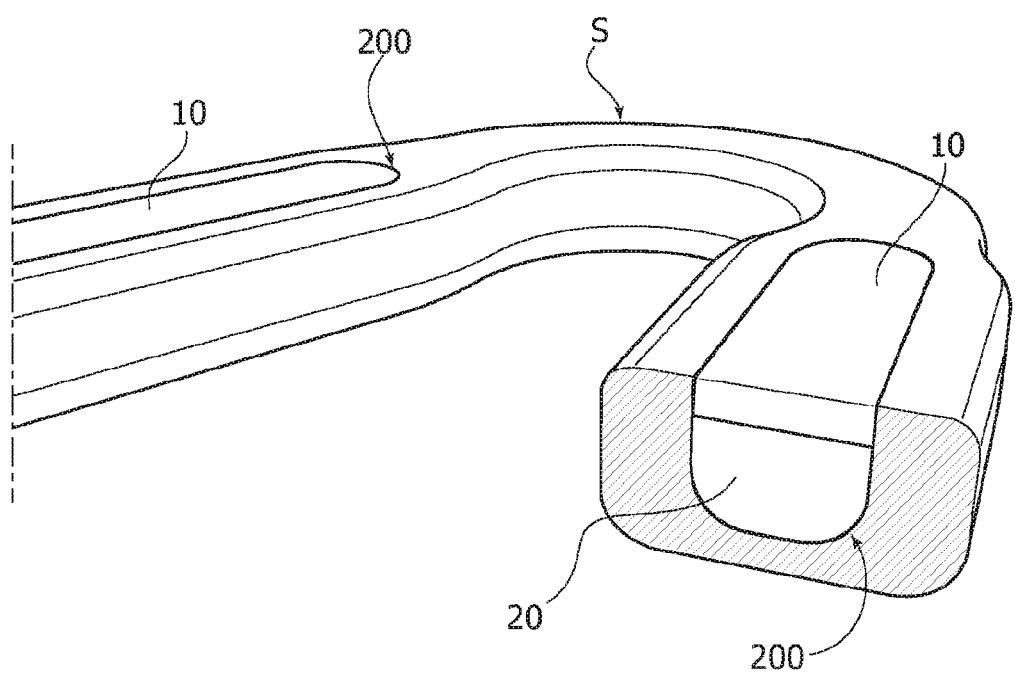

In one or more embodiments, as schematically represented in FIG. 10, the formulation 20 loaded into the recesses 200 may be subjected to a stabilization treatment, e.g. by heating, carried out, for example, by means of a timely jet of heated nitrogen NJ1.

The tablets of the formulation 10 can then be arranged above the formulation 20.

In one or more embodiments, this may be accomplished by an optical recognition software able to recognize the recess 200 and position the tablet in the recess with a mechanical arm. A mechanical arm of this type can be equipped with a metal probe with a timely jet of heated nitrogen NJ2 (identical or different from the jet NJ1) so as to thermally fix the tablet within the recess 200 of the stent e.g. making sure that the tablet, initially "narrower" (and possibly protruding above) than the recess 200 is widened so as to completely cover the formulation 20 (see the sequence of FIGS. 13 and 14).

It will be appreciated that in one or more embodiments, the modes exemplified here with reference to the formation of tablets with the formulation 10 and the loading of these tablets into the recesses 200 can also be applied to the formulation 20.

More generally, the modes exemplified here with reference to the formation of tablets of the formulation 10 and the loading of these tablets into the recesses 200 can be applied to any number (1, 2, . . . , N) of formulations.

In one or more embodiments, a method for loading at least one powder substance (e.g. 10) into recesses (200) provided at a stent (e.g. S) surface, may comprise:
  applying compression to said at least one powder substance to thereby form tablets insertable into said recesses (200),
  inserting said tablets into said recesses.

In one or more embodiments, this method can comprise:
  loading at least one additional substance (e.g. 20) into said recesses, by partially filling said recesses with said at least one additional substance, and
  inserting said tablets of said at least one substance into said recesses partially filled with said at least one additional substance.

In one or more embodiments, said at least one additional substance can comprise a powder substance.

In one or more embodiments, a method such as that considered here can comprise applying an optionally warm stabilization treatment, (e.g. NJ1) to said at least one additional substance that partially fills said recesses.

In one or more embodiments, a method such as that considered here can comprise applying a treatment (e.g. NJ2), for forming closing lids of said recesses, to said tablets of said at least one substance inserted into said recesses partially filled with said at least one additional substance.

In one or more embodiments, a method such as that considered here can comprise:
  producing said tablets of said at least one substance with dimensions smaller than said recesses, and
  applying a melting treatment (e.g. NJ2) to said tablets of said at least one substance inserted into said recesses partially filled with said at least one additional substance (20), whereby said at least one substance forms a closing lid of said recesses.

In one or more embodiments, a method such as that considered here can comprise applying an optionally warm fixation treatment to said tablets of said at least one substance inserted into said recesses.

In one or more embodiments, said at least one substance (e.g. 10) can comprise an anti-inflammatory active principle.

In one or more embodiments, said at least one additional substance (e.g. 20) can comprise an anti-proliferative active principle.

Example 6. Differential Scanning Thermal Analysis

Differential scanning calorimetry (DSC) measures temperatures and enthalpies associated with transitions of materials. This technique provides qualitative and quantitative information on the chemical and physical changes that are involved in endothermic or exothermic processes.

The analysis was carried out within a furnace in which the material to be analyzed, enclosed in an aluminum crucible, was heated and the temperature recorded was compared with that achieved by a blank reference aluminum crucible.

From the difference of temperature recorded compared to the blank, a thermogram is obtained showing peaks or transitions that highlight the changes of the physical-chemical state of the analyzed material.

The thermal analyzes were conducted on the formulations used for producing the stent of Example 3. The respective thermograms are shown in FIGS. 15 and 16.

The Sirolimus-stearic acid formulation with a drug:excipient weight ratio equal to 45:55 presents an endothermic phenomenon at 69° C. that indicates the melting point of the excipient (stearic acid) contained in the formulation and exploitable for the thermal fixing within the recesses of the cobalt-chrome stent (FIG. 15).

The formulation Dexamethasone acetate-stearic acid and palmitic acid with a drug:excipient weight ratio equal to 65:35 presents an endothermic phenomenon at 57° C. that indicates the melting point of the mixture of excipients contained in the formulation and exploitable for the thermal fixation within the recesses of the cobalt-chrome stent at the outermost layer (FIG. 16).

The difference in melting temperature of the mixtures of excipients used for producing the two formulations results as being greater than 10° C. and this allows the thermal stabilization treatment of the two formulations to be carried out.

The invention claimed is:

1. A method for loading at least two powder substances into recesses (200) provided at a stent (S) surface, the method comprising:
   applying compression (100) to at least one powder substance (10) to thereby form tablets insertable into said recesses (200),
   loading at least one additional substance (20) into said recesses (200), by partially filling said recesses (200) with said at least one additional substance, wherein said at least one additional substance (20) includes a powder substance and
   inserting said tablets of said at least one substance (10) into said recesses partially filled with said at least one additional substance (20), wherein
      said at least one substance (10) includes an active principle with anti-inflammatory activity mixed with at least one or more first excipients selected from linear or branched saturated fatty acids,
      said at least one additional substance (20) includes an active principle with anti-proliferative activity mixed with at least one or more second excipients selected from linear or branched saturated fatty acids,
   wherein said at least one first excipient or mixture of first excipients has a melting temperature lower than the melting temperature of said at least one second excipient or mixture of second excipients, and
   wherein the melting temperature of said at least one first excipient or mixture of first excipients is between 50° C. and 65° C. and the melting temperature of said at least one second excipient or mixture of second excipients is between 68° C. and 80° C., so that upon implantation of said stent to a patient said at least one substance (10) is released in less than about 5 days after implantation and said at least one additional substance (20) is released between 1 and 4 months after implantation.

2. The method of claim 1, including applying a stabilization treatment (NJ1) to said at least one additional substance (20) that partially fills said recesses.

3. The method of claim 2, wherein said stabilization treatment includes a heat treatment (NJ1) at a temperature T1, wherein said temperature T1 is between 68° C. and 80° C.

4. The method of claim 3, including applying a fixation treatment (NJ2) to said tablets of said at least one substance (10) inserted into said recesses (200), wherein the fixation treatment (NJ2) is a heat treatment at a temperature T2 and wherein said temperature T1 is greater than said temperature T2, wherein said temperature T2 is between 50° C. and 65° C.

5. The method of claim 4, wherein said temperature T1 is greater than said temperature T2 by at least 10° C.

6. The method of claim 4, wherein said temperature T1 is between 68° C. and 78° C. and said temperature T2 is between 54° C. and 60° C.

7. The method of claim 1, including applying a treatment (NJ2) providing closing lids of said recesses (200) to said tablets of said at least one substance (10) inserted into said recesses (200) partially filled with said at least one additional substance (20).

8. The method of claim 7, including:
   producing said tablets of said at least one substance (10) with dimensions smaller than said recesses (200), and
   applying a melting treatment (NJ2) to said tablets of said at least one substance (10) inserted into said recesses (200) partially filled with said at least one additional substance (20), whereby said at least one substance (10) forms a closing lid of said recesses.

9. The method of claim 1, including applying a fixation treatment (NJ2) to said tablets of said at least one substance (10) inserted into said recesses (200).

10. The method of claim 9, wherein the fixation treatment (NJ2) is a heat treatment at a temperature T2, wherein said temperature T2 is between 50° C. and 65° C.

11. A method for loading a powder substance into recesses (200) provided at a stent (S) surface, the method comprising:
   i) providing a tablet insertable into said recesses (200) comprising at least one powder substance (10), wherein said tablet has been formed by applying compression (100) to said at least one powder substance (10);
   ii) loading at least one additional substance (20) into said recesses (200), by partially filling said recesses (200) with said at least one additional substance, wherein said at least one additional substance (20) includes a powder substance;
   iii) subjecting the stent obtained in step ii) to a heat treatment at a temperature T1 for stabilizing the at least one additional substance (20) loaded on the stent;
   iv) inserting said tablets of said at least one substance (10) into said recesses partially filled with said at least one additional substance (20);
   v) subjecting the stent obtained in step iv) to a heat treatment at a temperature T2 whereby said at least one substance (10) forms a closing lid of said recesses;
   wherein
      aid at least one substance (10) includes an active principle with anti-inflammatory activity mixed with at least one or more first excipients selected from linear or branched saturated fatty acids comprising a number of carbon atoms between 4 and 18,
      said at least one additional substance (20) includes an active principle with anti-proliferative activity mixed with at least one or more second excipients selected from linear or branched saturated fatty acids comprising a number of carbon atoms between 16 and 34,
   wherein said at least one first excipient or mixture of first excipients has a melting temperature lower than the melting temperature of said at least one second excipient or mixture of second excipients,
   wherein the temperature T1 is greater than the temperature T2, and wherein said temperature T1 is between 68° C. and 80° C. and said temperature T2 is between 50° C. and 65° C.

12. The method of claim 11, wherein said temperature T1 is greater than said temperature T2 by at least 10° C.

13. The method of claim 11, wherein said temperature T1 is between 68°C. and 78° C. and said temperature T2 is between 54°C. and 60° C.

* * * * *